United States Patent
Speier et al.

(10) Patent No.: US 6,291,995 B1
(45) Date of Patent: Sep. 18, 2001

(54) APPARATUS AND METHOD FOR GENERATING A PULSE SEQUENCE

(75) Inventors: Peter Speier; Ralf Heidler, both of Stafford, TX (US)

(73) Assignee: Schlumberger Technology Corporation, Houston, TX (US)

(*) Notice: Subject to any disclaimer, the term of this patent is extended or adjusted under 35 U.S.C. 154(b) by 0 days.

(21) Appl. No.: 09/186,721

(22) Filed: Nov. 5, 1998

Related U.S. Application Data

(63) Continuation-in-part of application No. 09/033,965, filed on Mar. 3, 1998.

(51) Int. Cl.⁷ .......................................... G01V 3/00
(52) U.S. Cl. ............................. 324/303; 324/322
(58) Field of Search .................... 324/303, 300, 324/312, 314, 306, 307, 309, 318, 322

(56) References Cited

U.S. PATENT DOCUMENTS

| | | |
|---|---|---|
| 4,350,955 | 9/1982 | Jackson et al. . |
| 4,412,179 | * 10/1983 | Brown .................... 324/303 |
| 4,714,881 | 12/1987 | Givens . |
| 4,717,878 | 1/1988 | Taicher et al. . |
| 4,949,045 | 8/1990 | Clark et al. . |
| 5,023,551 | 6/1991 | Kleinberg et al. . |
| 5,055,787 | 10/1991 | Kleinberg et al. . |
| 5,212,447 | 5/1993 | Paltiel . |
| 5,280,243 | 1/1994 | Miller . |
| 5,363,041 | 11/1994 | Sezginer . |
| 5,381,092 | 1/1995 | Freedman . |
| 5,432,447 | 7/1995 | MacInnis et al. . |
| 5,451,873 | 9/1995 | Freedman et al. . |
| 5,557,201 | 9/1996 | Kleinberg et al. . |
| 5,596,274 | 1/1997 | Sezginer . |
| 5,705,927 | 1/1998 | Sezginer et al. . |
| 5,757,186 | 5/1998 | Taicher et al. . |
| 5,767,674 | 6/1998 | Griffin et al. . |
| 5,796,252 | 8/1998 | Kleinberg et al. . |

FOREIGN PATENT DOCUMENTS

| | | |
|---|---|---|
| 0 237 323 | 3/1987 | (EP) . |
| 2 310 500 A | 8/1997 | (GB) . |
| 2 311 139 A | 9/1997 | (GB) . |
| 2 311 864 A | 10/1997 | (GB) . |
| WO 92/07279 | 4/1992 | (WO) . |
| WO 98/29639 | 7/1998 | (WO) . |

OTHER PUBLICATIONS

R. S. Dembo and U. Tulowitzki, "On the Minimization of Quadratic Functions Subjects to Box Constraints," Yale Univ. School of Organization and Management, SOM Working Paper Series B #71, New Haven (1983).

* cited by examiner

*Primary Examiner*—Louis Arana
(74) *Attorney, Agent, or Firm*—John J. Ryberg; Brigitte L. Jeffery

(57) ABSTRACT

The present invention is directed to a method for generating a pulse sequence using a logging tool. A pulse programmer is provided for adaptively controlling the creation and application of a sequence of RF magnetic field pulses to an earth formation. In order to control the RF pulses, a portion of a memory device is partitioned into a plurality of tables and control information is stored in the tables. The pulse programmer creates the pulse sequence using information found in the memory device and the operating conditions of the tool. The structure of the partitioned memory device allows the pulse programmer to adapt and change the timing of the pulse sequences autonomously downhole.

29 Claims, 12 Drawing Sheets

APPARATUS AND METHOD FOR GENERATING A PULSE SEQUENCE

CROSS-REFERENCES

This is a continuation-in-part of U.S. patent application Ser. No. 09/033,965, filed Mar. 3, 1998.

BACKGROUND OF THE INVENTION

The present invention relates generally to an apparatus and method for measuring nuclear magnetic resonance properties of an earth formation traversed by a borehole, and more particularly, to an apparatus and method for generating a pulse sequence.

It is well recognized that atomic particles of an earth formation having non-zero nuclear spin magnetic moment, for example protons, have a tendency to align with a static magnetic field imposed on the formation. Such a magnetic field may be naturally generated, as is the case for the earth's magnetic field, $B_E$. An RF pulse applying a second magnetic field transverse to $B_E$ creates a magnetization component in the transverse plane as (perpendicular to $B_E$) which precesses about the $B_E$ vector with a characteristic resonance known as the Larmor frequency, $\omega_L$, which depends on the strength of the static magnetic field and the gyromagnetic ratio of the particle. Hydrogen nuclei (protons) precessing about a magnetic field $B_E$ of 0.5 gauss, for example, have a characteristic frequency of approximately 2 kHz. If a population of hydrogen nuclei were made to precess in phase, the combined magnetic fields of the protons can generate a detectable oscillating voltage in a receiver coil, conditions known to those skilled in the art as free induction decay or a spin echo. Hydrogen nuclei of water and hydrocarbons occurring in rock pores produce nuclear magnetic resonance (NMR) signals distinct from signals arising from other solids.

U.S. Pat. No. 4,717,878 issued to Taicher et al. and U.S. Pat. No. 5,055,787 issued to Kleinberg et al., describe NMR tools which employ permanent magnets to polarize hydrogen nuclei and generate a static magnetic field, $B_0$, and RF antennas to excite and detect nuclear magnetic resonance to determine porosity, free fluid ratio, and permeability of a formation. The atomic nuclei align with the applied field, $B_0$, with a time constant of $T_1$. After a period of polarization, the angle between the nuclear magnetization and the applied field can be changed by applying an RF field, $B_1$, perpendicular to the static field $B_0$, at the Larmor frequency $f_L = \gamma B_0/2\pi$, where $\gamma$ is the gyromagnetic ratio of the proton and $B_0$ designates the static magnetic field strength. After termination of the RF pulse, the protons precess in the plane perpendicular to $B_0$. A sequence of refocusing RF pulses generates a sequence of spin-echoes which produce a detectable NMR signal in the antenna.

U.S. Pat. No. 5,280,243 issued to Melvin Miller describes a nuclear magnetic resonance tool for formation evaluation while drilling. The tool includes a probe section consisting of a permanent magnet disposed in a longitudinally extending annular recess outside the drill collar and an antenna disposed on a non-conductive magnetic sleeve outside the drill collar. The gradient of the static magnetic field magnitude is in the radial direction. The antenna produces an RF magnetic field substantially perpendicular to both the longitudinal axis of the tool and the static field direction. With the '243 apparatus, the magnet must be long in axial extent compared to its diameter for the magnetic fields to approximate its intended 2-D dipole behavior.

U.S. Pat. No. 5,757,186 issued to Taicher et al. describes a measurement-while-drilling tool which includes a sensing apparatus for making nuclear magnetic resonance measurements of the earth formation. The NMR sensing apparatus is mounted in an annular recess formed into the exterior surface of the drill collar. In one embodiment, a flux closure is inserted into the recess. A magnet is disposed on the outer radial surface of the flux closure. The magnet is constructed from a plurality of radial segments which are magnetized radially outward from the longitudinal axis of the tool. The flux closure is required to provide suitable directional orientation of the magnetic field.

The tools disclosed in the '243 and '186 patents suffer from common problems: both tools require using a nonconductive magnet and placing the magnet outside the drill collar. For the '243 tool, the outside surface of the drill collar must contain a recessed area to accommodate the nonconductive magnet. For the '186 tool, the outside surface of the drill collar must contain a recessed area to accommodate the flux closure, nonconductive magnet, and antenna. Because the strength of the drill collar is a function of its radii, reducing the external diameter to accommodate the magnet only or the flux closure, magnet, and antenna results in an unacceptably weak section of the drill collar which may bend or break during the drilling operation.

U.S. Pat. No. 5,557,201 issued to Kleinberg et al. describes a pulsed nuclear magnetism tool for formation evaluation while drilling. The tool includes a drill bit, drill string, and a pulsed nuclear magnetic resonance device housed within a drill collar made of nonmagnetic alloy. The tool includes a channel, within the drill string and pulsed NMR device, through which drilling mud is pumped into the borehole. The pulsed NMR device comprises two tubular magnets, which are mounted with like poles facing each other, surrounding the channel, and an antenna coil mounted in an exterior surface of the drill string between the magnets. This tool is designed to resonate nuclei at a measurement region known to those skilled in the art as the saddle point.

U.S. Pat. No. 5,705,927 issued to Sezginer et al. also describes a pulsed nuclear magnetism tool for formation evaluation while drilling. The tool includes shimming magnets, located either inside or outside the tool, which suppress the magnetic resonance signal of the borehole fluids by raising the magnitude of the static magnetic field in the borehole so that the Larmor frequency in the borehole is above the frequency of the oscillating field produced by an RF antenna located in a recessed area of the tool. The shimming magnets also reduce the gradient of the static magnetic field in the region of investigation.

SUMMARY OF THE INVENTION

A substantially axisymmetric static magnetic field is generated in a formation traversed by a borehole. A pulse programmer is provided for adaptively controlling the creation and application of a sequence of RF magnetic field pulses to the formation. In order to control the RF pulses, a portion of a memory device is partitioned into a plurality of tables and control information is stored in the tables. The tables may include the following: a buffer table which describes the layout of stacking buffers, an acquisition table which defines the acquired signals accumulated in buffers, a filter coefficient table which prescribes the detection filter employed with a signal acquisition, a spin dynamics correction table which designates the spin dynamics correction to be used for each buffer, and a data processing table which designates the nuclear magnetic resonance characteristic calculated from the acquired buffers. In addition to the pulse programmer, other tasks may share the control information stored in the tables.

The pulse programmer further comprises a pulse sequence template, used for generating pulse sequences, which includes a sequence of states dependent on repetition and timing variables. These variables are calculated from sequence configuration parameters using a calculation block. The timing variables include the wait time, the echo spacing, and the number of acquired echoes. The configuration parameters include the duration of an excitation pulse, the pulse amplitude, and the pulse shape. The sequence of states further comprises a plurality of alternative states for portions of the pulse sequence. In real time, one of the alternative states may be selected based on external conditions of the apparatus.

BRIEF DESCRIPTION OF THE DRAWINGS

The advantages of the present invention will become apparent from the following description of the accompanying drawings. It is to be understood that the drawings are to be used for the purpose of illustration only, and not as a definition of the invention.

In the drawings.

DETAILED DESCRIPTION OF THE PREFERRED EMBODIMENT

Figure 1:
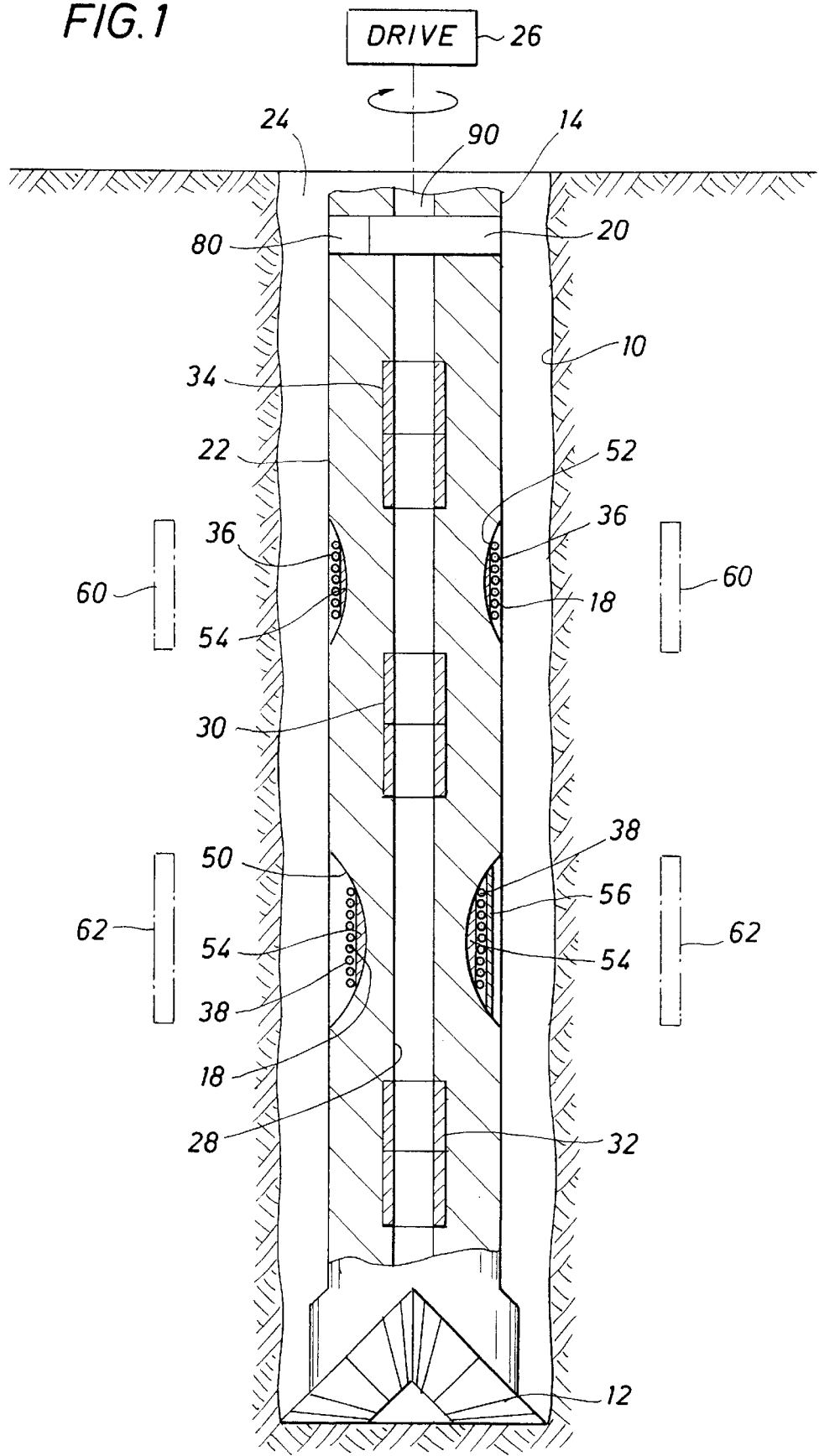
FIG. 1 illustrates a logging-while-drilling apparatus.

Referring to FIG. 1, a nuclear magnetic resonance (NMR) logging-while-drilling tool 10 is illustrated. The tool 10 comprises a drill bit 12, drill string 14, a plurality of RF antennas 36, 38, and at least one gradient coil 56. The tool 10 further comprises electronic circuitry 20 housed within the drill collar 22. The electronic circuitry 20 comprises RF resonance circuitry for the antennas 36, 38, a microprocessor, a digital signal processor, and a low voltage bus. The tool 10 further comprises a plurality of tubular magnets 30, 32, and 34 which are polarized in a direction parallel to the longitudinal axis of the tool 10 but opposite to each other, i.e., with like magnetic poles facing each other. The magnets 30, 32, and 34 comprise either a conductive or nonconductive material. The configuration of magnets 30, 32, and 34 and antennas 36, 38 provides for at least two NMR regions of investigation 60, 62 with a substantially axisymmetric static and RF magnetic field.

A means for drilling a borehole 24 in the formation comprises drill bit 12 and drill collar 22. The drill collar 22 may include a stabilizing means (not shown) for stabilizing radial motion of the tool 10 in the borehole during drilling, however, the stabilizing means is not required; therefore, the tool 10 may operate unstabilized or stabilized. Mud flow sleeve 28 defines a channel 90 for carrying the drilling fluid through the drill string 14. A drive mechanism 26 rotates the drill bit 12 and drill string 14. This drive mechanism is adequately described in U.S. Pat. No. 4,949,045 issued to Clark et al. However, a downhole mud motor may be placed in the drill string as the drive mechanism 26.

It is within contemplation of the subject invention to combine N+1 magnets to obtain at least N regions of investigation in the formation. The combinations contemplated by this invention include, but are not limited to, a low gradient-low gradient, high gradient-high gradient, high gradient-low gradient, low gradient-high gradient, or a combination of high gradient, low gradient, and saddle point regions. The combination of high and low gradient static field regions in the formation offers several advantages. For example, the high gradient region may have a higher signal-to-noise ratio but may experience signal loss when the tool 10 undergoes lateral motion in the borehole. On the other hand, the low gradient region has lower susceptibility to signal loss problems when the tool 10 is in motion. Also, with moderate tool motion, longer echo trains can be acquired in the low gradient region than in the high gradient region thereby providing more information about permeability, bound and free fluid, and hydrocarbon types. Moreover, the combination of data acquired with both gradient regions may provide quantitative information about the amount of lateral motion the tool 10 experiences and can be used to motion correct the NMR data, or, at least, quality control the data. Measurements of devices, such as strain gauges, accelerometers, or magnetometers, or any combinations of these devices, may be integrated with NMR information to quality control the data or make corrections to the spin-echo train. With the combination of high and low gradient static magnetic fields, the high gradient region exhibits more diffusion effect and therefore is of greater interest for hydrocarbon typing techniques than the low gradient region. Finally, the low gradient region has a static magnetic field having a low amplitude and therefore, this region with its lower Larmor frequency is less affected by formation and borehole fluid conductivity.

Low Gradient Sonde

Figure 2:
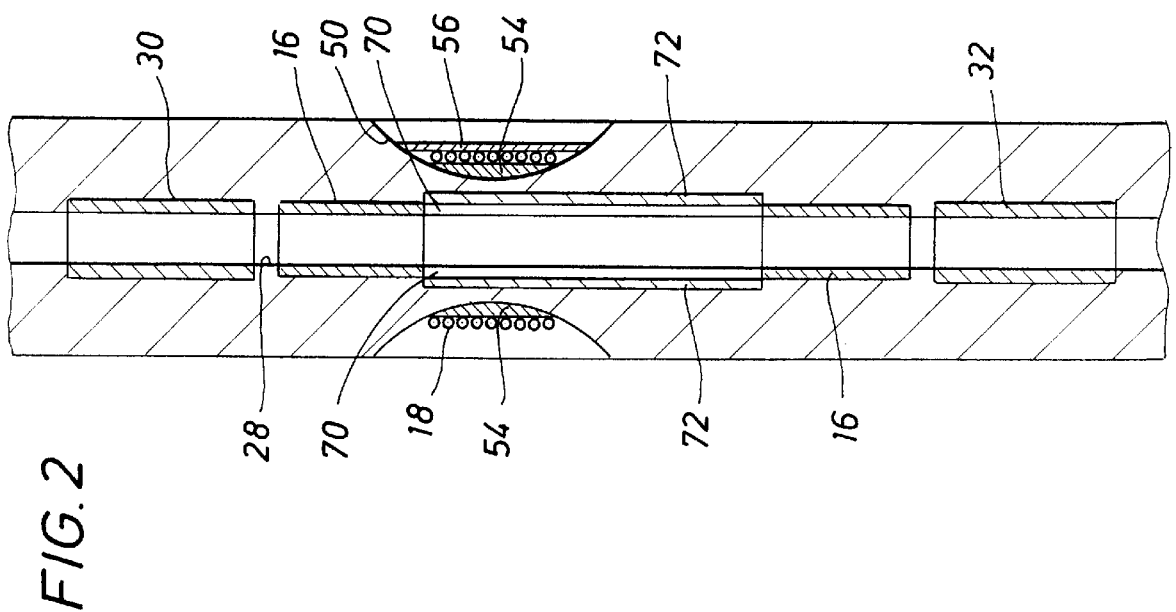
FIG. 2 depicts the low gradient sonde.
Figure 2A:
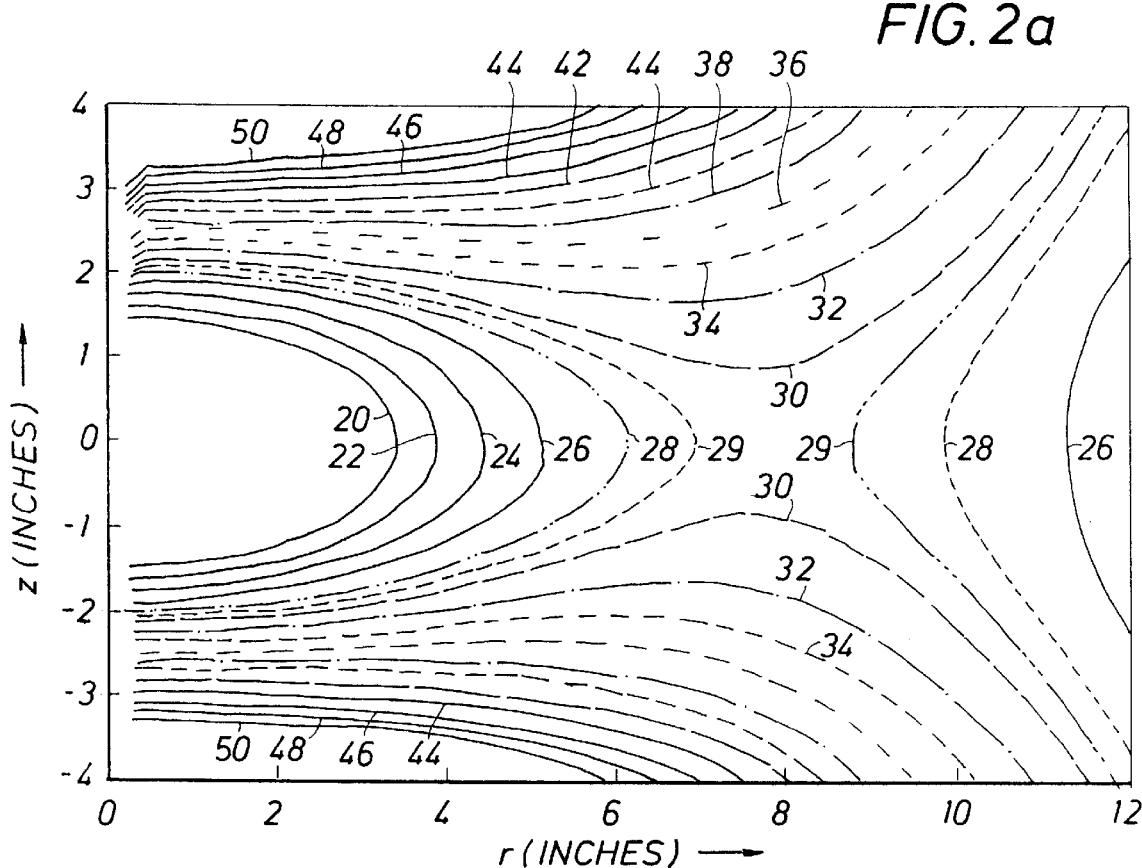
FIGS. 2a–2d illustrate the contour lines $|\vec{B}_o|$ corresponding to four low gradient magnet configurations.
Figure 2B:
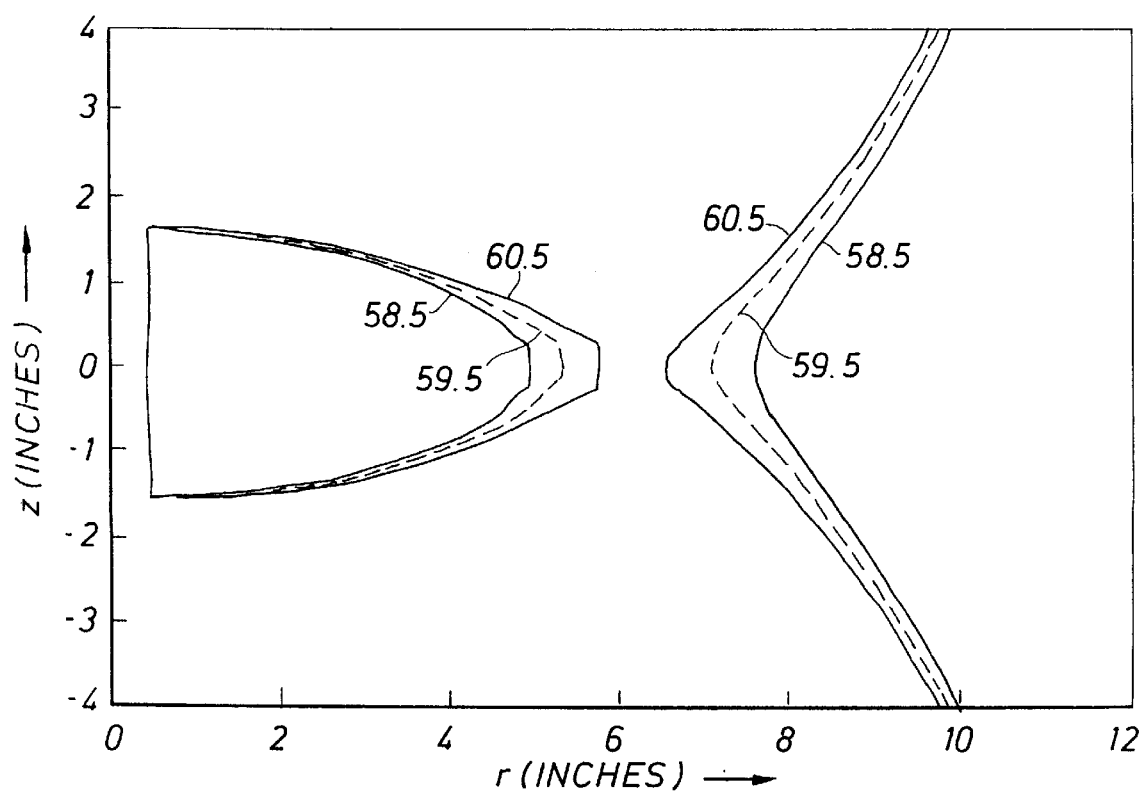

Referring to FIG. 2, in one section of the tool, hereinafter referred to as the low gradient sonde, a central magnet 30 is axially separated from a lower magnet 32. These magnets 30, 32 generate a substantially axisymmetric static magnetic field that is radial in its polarization and, over a reasonably long cylindrical shell, the static magnetic field has a fairly constant magnitude. It is within contemplation of the subject invention to excite a plurality of cylindrical shells of spins in the formation where each shell is resonant at a different RF frequency, and to sequentially interrogate each shell with sequences of RF pulses.

The area between magnets 30, 32 is suitable for housing elements such as electronic components, an RF antenna, and other similar items. For example, a plurality of electronic pockets 70 may form an integral part of the mud sleeve 28. These pockets 70 may house the RF circuitry (e.g., Q-switch, duplexer, and pre-amplifier), preferably in close proximity of the RF antenna. In a preferred embodiment of the invention, the pockets 70 form an integral part of magnetically permeable member 16. In that case, to maintain the axial symmetry of the magnetic field, a highly magnetically permeable cover 72 is located over each pocket 70.

The magnetically permeable member 16 is positioned inside the drill collar 22 between the magnets 30, 32.

Member 16 may consist of a single piece or a plurality of sections combined between the magnets 30, 32. Member 16 is constructed of a suitable magnetically permeable material, such as ferrite, permeable steel or another alloy of iron and nickel, corrosion resistant permeable steel, or permeable steel having a structural role in the member design, such as 15-5 Ph stainless steel. The magnetically permeable member 16 focuses the magnetic field and may also either carry drilling fluid through the drill string or provide structural support to the drill collar. Further, member 16 improves the shape of the static magnetic field generated by magnets 30, 32 and minimizes variations of the static magnetic field due to vertical and lateral tool motion during the period of acquiring the NMR signal. The segment of sleeve 28 between magnets 30, 32 may comprise magnetically permeable member 16. In that case, the segments of sleeve 28 under magnets 30, 32 shall consist of a non-magnetic member. Alternatively, a magnetically permeable chassis surrounding the segment of sleeve 28 between magnets 30, 32 defines member 16. In this case, the segment may consist of a magnetic or non-magnetic material. It is within contemplation of this invention to integrate the chassis and segment to form member 16.

The magnets 30, 32 are polarized in a direction parallel to the longitudinal axis of the tool 10 with like magnetic poles facing each other. For each magnet 30, 32, the magnetic lines of induction travel outward from an end of the magnet 30, 32 into the formation, along the axis of the tool 10, and travel inward to the other end of the magnet 30, 32. In the region between central magnet 30 and lower magnet 32, the magnetic lines of induction travel from the center outward into the formation, creating a static field in a direction substantially perpendicular to the axis of the tool 10. The magnetic lines of induction then travel inward symmetrically above the central magnet 30 and below the lower magnet 32 and converge in the longitudinal direction inside sleeve 28. Because of the separation, the magnitude of the static magnetic field in the central region between the central 30 and lower 32 magnet is spatially homogeneous in comparison to a saddle-point field.

The amount of separation between the magnets 30, 32 is determined based on several factors: (1) selecting the requisite magnetic field strength and homogeneity characteristics; (2) generating a field having small radial variations in the region of interest so that the echoes received during a pulse sequence (i.e., CPMG, CPI, or other sequences) are less sensitive to lateral tool motion; (3) depth of investigation; and (4) minimizing interference between the resonance circuitry and the low voltage telemetry bus in order to improve isolation of the receiving antenna which detects NMR signals from the formation. As the separation between the magnets 30, 32 decreases, the magnetic field becomes stronger and less homogeneous. Conversely, as the separation between the magnets 30, 32 increases, the magnetic field becomes weaker and more homogenous.

FIGS. 2a–2d illustrate the contour lines of $|\vec{B}_0|$ corresponding to four laboratory modeled configurations of central 30 and lower 32 magnets. These modeled results were computed using a tool having a preselected diameter (a constant diameter was used for modeling all configurations). The configuration corresponding to FIG. 2a comprises a non-magnetically permeable member separating a central 30 and lower 32 magnet by 25 inches. The configuration corresponding to FIG. 2b comprises a non-magnetically permeable member separating a central 30 and lower 32 magnet by 18 inches. The configuration corresponding to FIG. 2c comprises a non-magnetically permeable member separating a central 30 and lower 32 magnet by eight inches. The low gradient sonde, corresponding to FIG. 2d, comprises a magnetically permeable member 16 separating a central 30 and lower 32 magnet by 25 inches. The aforementioned dimensions were modeled to merely illustrate the affect of distance and/or a magnetically or non-magnetically permeable member on $|\vec{B}_0|$. FIGS. 3a–3d represent the contour lines of the gradient $|\nabla B_0|$ corresponding respectively to configurations illustrated in FIGS. 2a–2d.

Figure 3A:
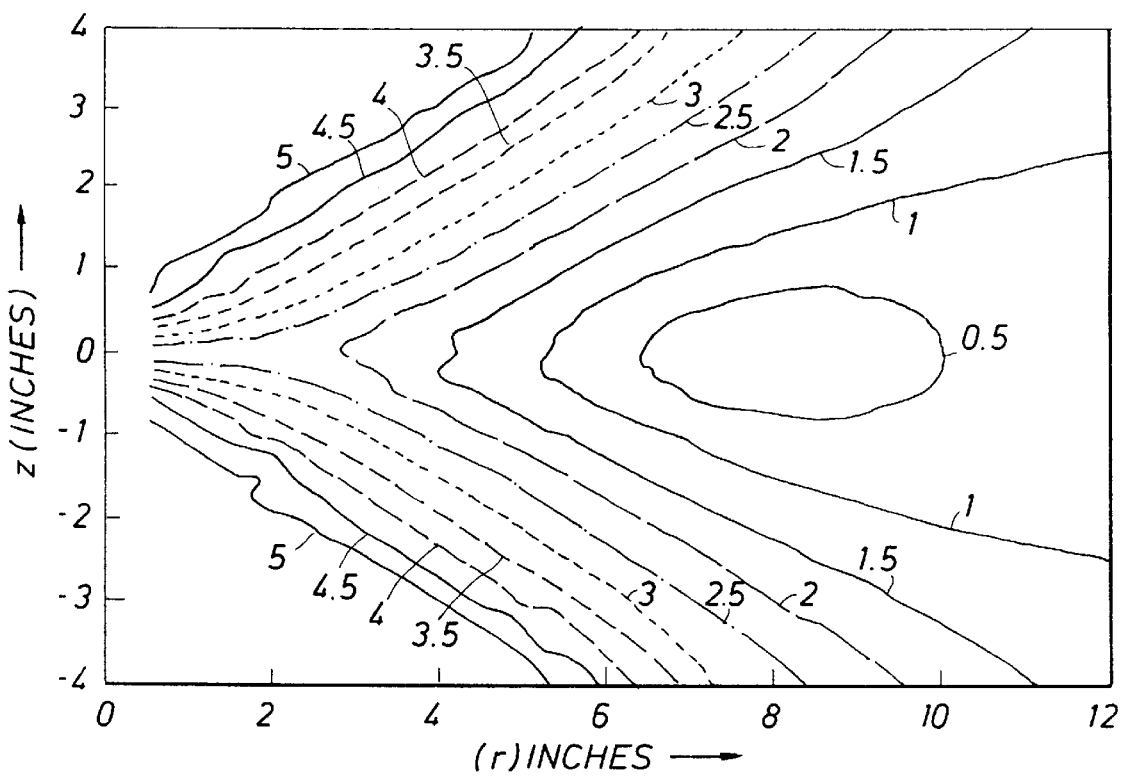
FIGS. 3a–3d represent the contour lines of the gradient $|\nabla B_0|$ corresponding to four low gradient magnet configurations.
Figure 3B:
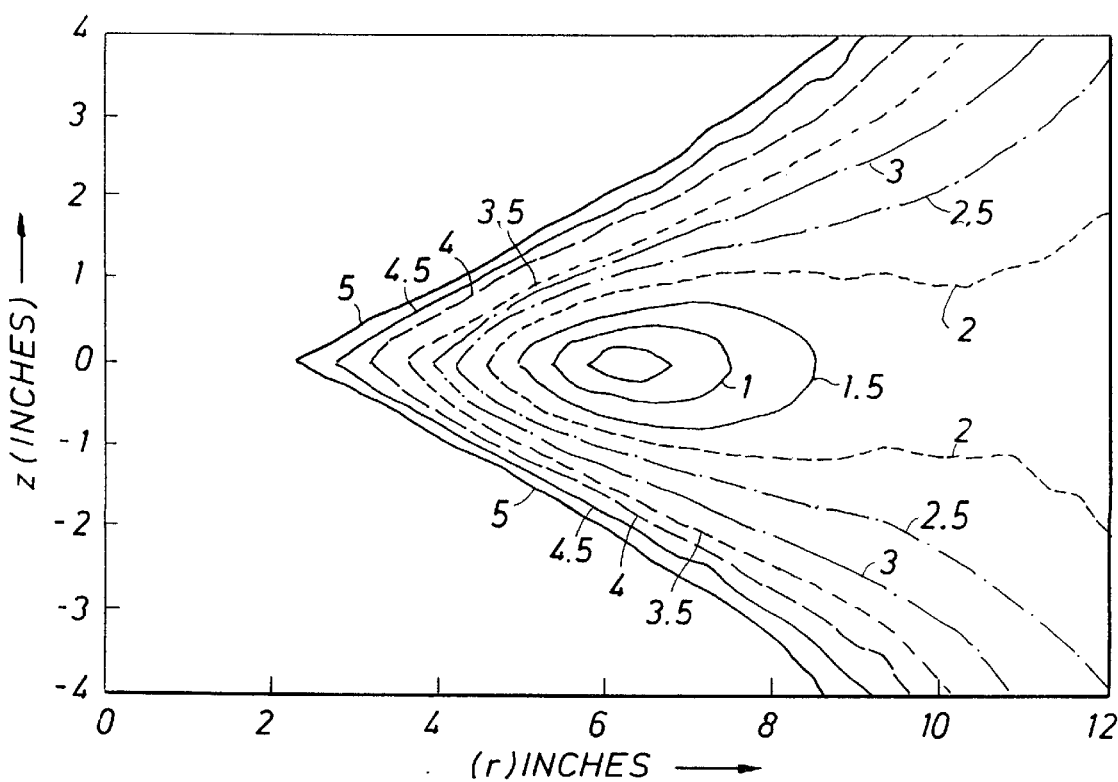
Figure 3C:
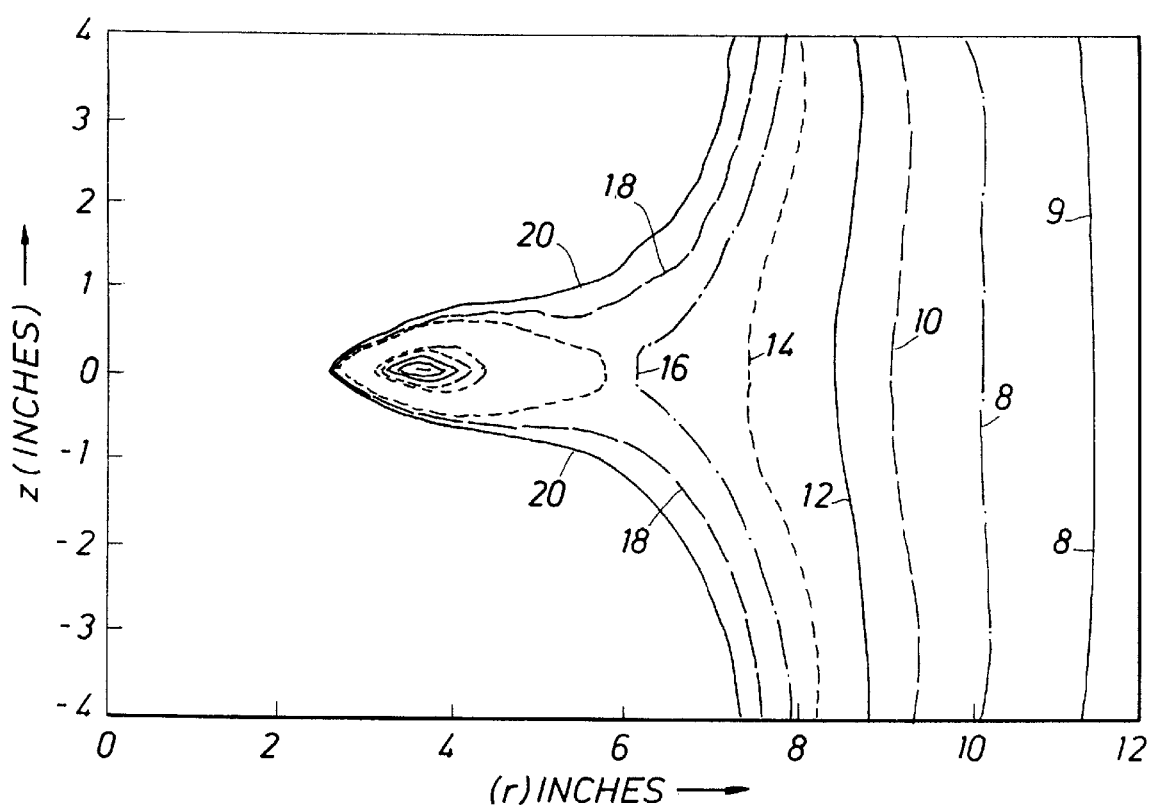
Figure 3D:
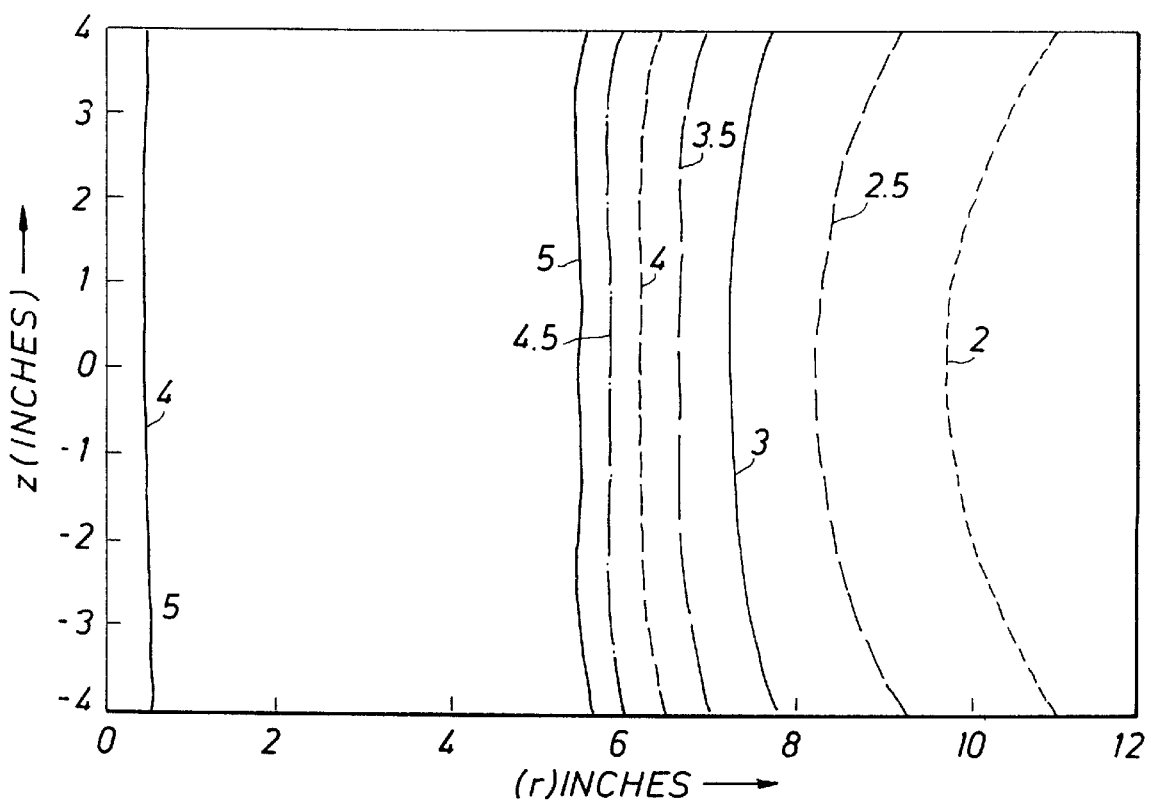

In the low gradient sonde, the magnetically permeable member 16 shunts a significant portion of the magnetic flux into the center of the tool 10. To illustrate, the magnitude of the $B_0$ field shown in FIG. 2d at a distance of approximately seven inches radially from the longitudinal axis of tool 10 is twice as large as the $B_0$ field shown in FIG. 2a which was generated by the same magnet configuration separated by a non-magnetically permeable member. Furthermore, the low gradient sonde produces a longer and more uniform extent of the static magnetic field in the axial direction. The NMR signal measured in this section of the tool is substantially less sensitive to the vertical motion of the tool. Referring to FIG. 3d, with the low gradient sonde, a relatively small, approximately 3 Gauss/cm, gradient is measured at a distance of approximately seven inches radially from the longitudinal axis of tool. This low gradient results in a measured NMR signal which is substantially less sensitive to the lateral motion of the tool 10. When motion is moderate, longer echo trains may be acquired in this region thereby providing more information about permeability, bound and free fluid, and hydrocarbon types. In the case of the low gradient sonde, as with other gradient designs, the proton rich borehole region surrounding the tool 10 will resonate only at frequencies higher than those being applied to the volume of investigation, i.e., there is no proton borehole signal. Other NMR sensitive nuclei found in drilling mud, such as sodium-23, resonate at significantly higher static magnetic field strengths than hydrogen when excited at the same RF frequency. For the low gradient sonde, these higher field strengths are not produced in the borehole region surrounding the tool or near the antenna where such unwanted signals could be detected.

High Gradient Sonde

Figure 4:
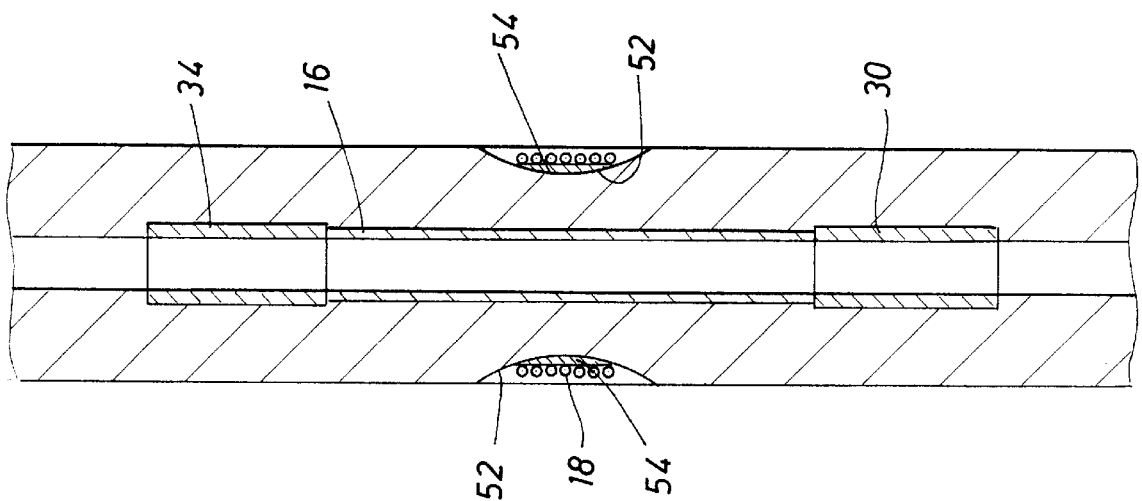
FIG. 4 depicts the high gradient sonde.

Referring to FIG. 4, in another section of the tool, hereinafter referred to as the high gradient sonde, a central magnet 30 is axially separated from an upper magnet 34. The magnets 30, 34 are polarized in a direction parallel to the longitudinal axis of the tool 10 with like magnetic poles facing each other. These magnets 30, 34 generate a substantially axisymmetric static magnetic field that is radial in its polarization and, over a reasonably long cylindrical shell, the static magnetic field has a fairly constant magnitude. It is within contemplation of the subject invention to excite a plurality of cylindrical shells of spins in the formation where each shell is resonant at a different RF frequency.

Figure 2C:
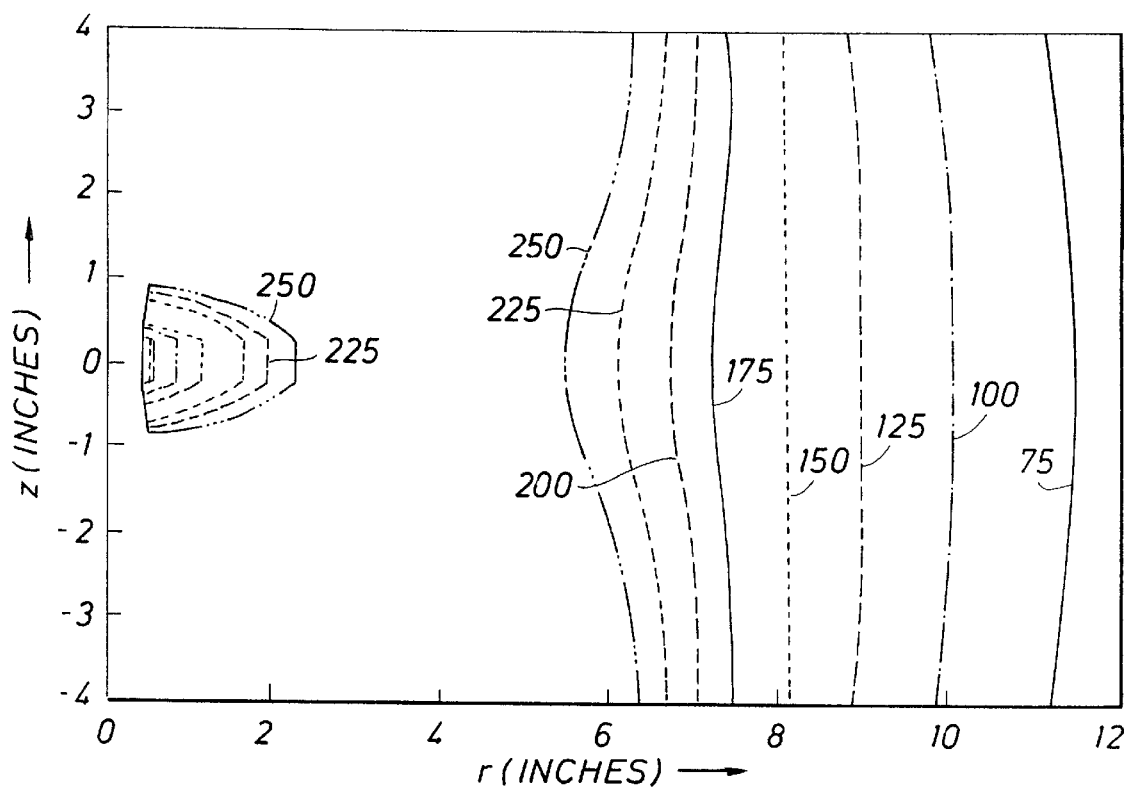
Figure 2D:
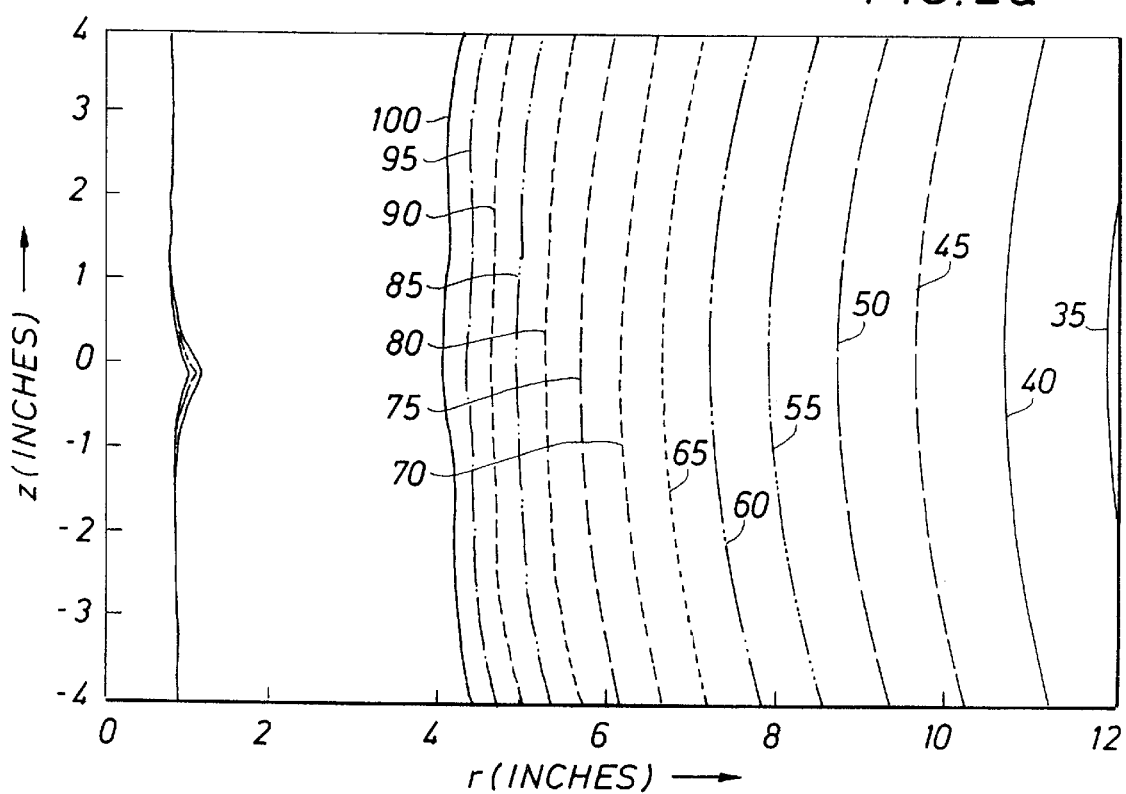

As illustrated in FIG. 2c, if the magnet separation between 30 and 34 is approximately eight inches, the contour lines of the static magnetic field strength are substantially straight and the strength of $|\vec{B}_0|$ is greater than the static magnetic field strength of the low gradient region. However, the gradient $|\nabla B_0|$ becomes larger, as illustrated in FIG. 3c, at a distance of approximately seven inches radially from the longitudinal axis of the tool. The contour lines of $|\nabla B_0|$ are curved denoting variation of the gradient in the axial direction.

Figure 4A:
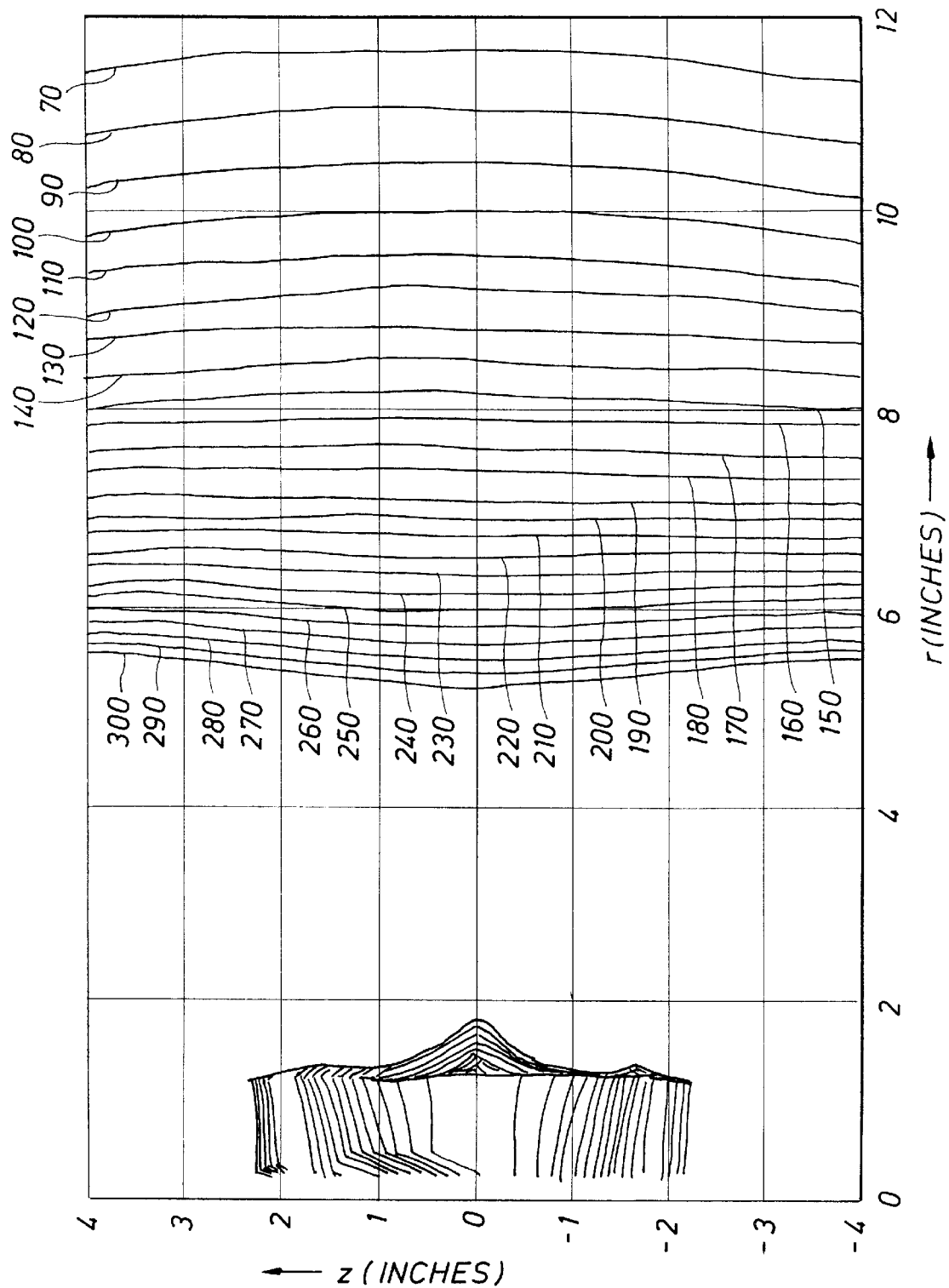
FIG. 4a represents the contour lines $|\vec{B}_o|$ corresponding to the high gradient magnet configuration.
Figure 4B:
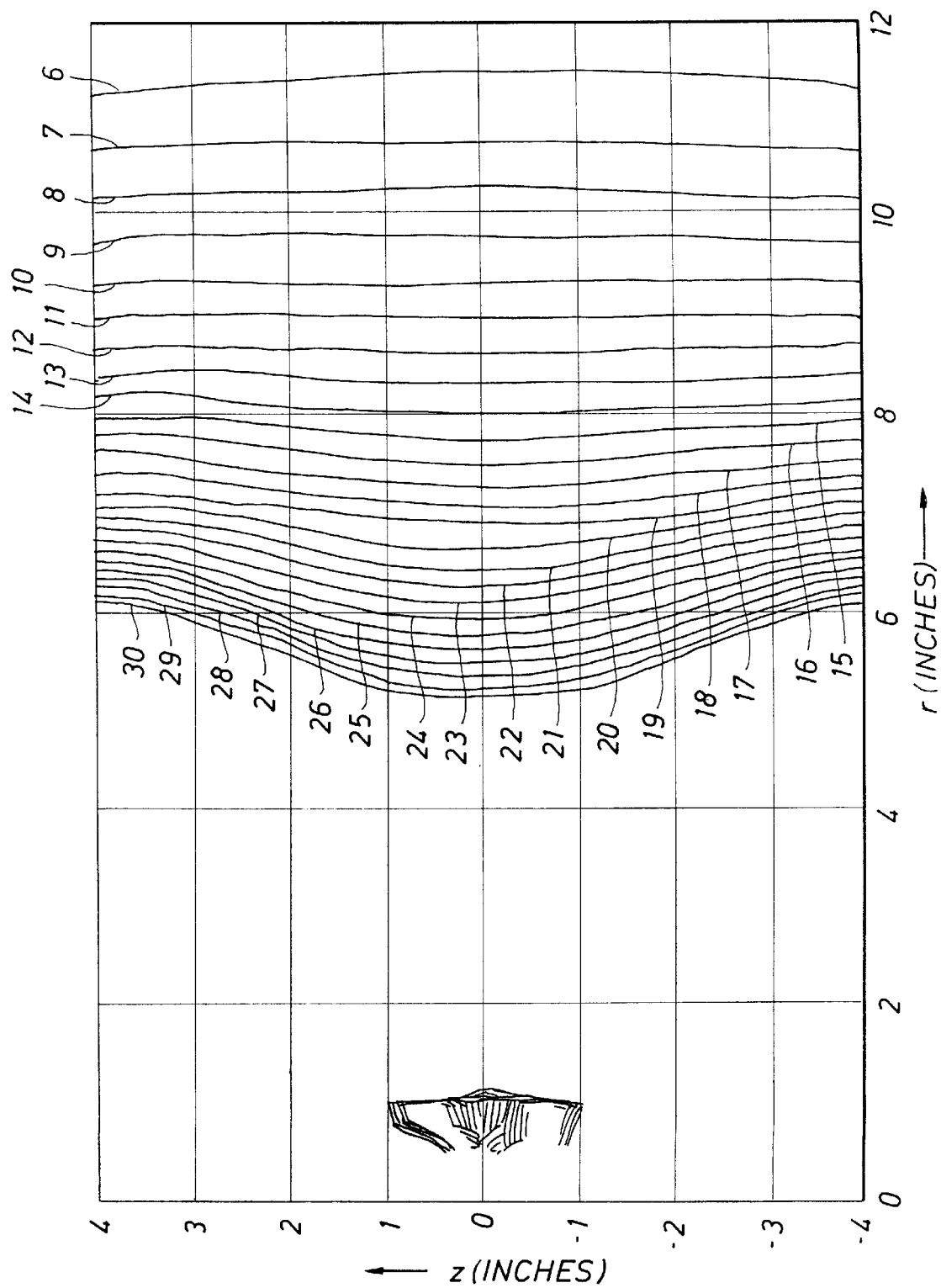
FIG. 4b represents the contour lines of the gradient $|\nabla B_0|$ corresponding to the high gradient magnet configuration.

The high gradient sonde is improved by inserting a magnetically permeable member 16 between magnets 30, 34. FIG. 4a represents contour lines of $|\vec{B}_0|$ corresponding to a configuration where magnetically permeable member 16 separates the upper 34 and central 30 magnets by eight inches. The contour lines of FIG. 4a show a slightly stronger field indicating a better signal-to-noise ratio and less curvature in the axial direction than the contour lines of FIG. 2c. Also, as illustrated in FIG. 4b, the magnetically permeable member 16 produces a more constant gradient $|\nabla B_0|$ in the axial direction that may simplify interpretation of the NMR measurements influenced by diffusion.

In the case of the high gradient sonde, as with other gradient designs, the proton rich borehole region surrounding the tool 10 will resonate only at frequencies higher than those being applied to the volume of investigation, i.e., there is no proton borehole signal. The high gradient sonde is sensitive to a small part of the sodium from the borehole fluid. For a 30% NaCl concentration borehole fluid, possibly the worst case, the error of the estimated porosity due to the sodium signal is approximately 0.08 pu. In the low gradient sonde, the sodium signal is substantially smaller than in the high gradient sonde. Consequently, the sodium signal is negligible for both NMR sondes.

Antennas and Gradient Coils

Referring to FIGS. 2 and 4, an RF magnetic field is created in the regions of investigation by antennas 36, 38 which are provided in recessed areas 50, 52. The RF field may be produced by one or more RF antenna segments that transmit and/or receive from different circumferential sectors of the logging device. See U.S. patent application Ser. Nos. 08/880,343 and 09/094,201 assigned to Schlumberger Technology Corporation. Preferably, each antenna 36, 38 comprises a coil 18 wound circumferentially around the recessed area 50, 52. The RF field created by such a coil arrangement is substantially axisymmetric. It is within contemplation of the subject invention to utilize the antenna 36, 38 for detecting NMR signals. However, a separate antenna or receiver may be used to detect the signals. A non-conductive material 54 is provided in the recessed area 50, 52 beneath the antenna 36, 38. The material 54 is preferably a ferrite to increase the efficiency of the antenna 36, 38. Alternatively, the material 54 may comprise plastic, rubber, or a reinforced epoxy composite material. The antennas 36, 38 are resonated by RF circuitry to create an RF magnetic field in the regions of investigation.

The recessed area 52 forms a shallow groove in the drill collar without reducing the inner diameter of the drill collar, which is ordinarily done to increase strength in a region of drill collar where the outer diameter has been recessed to provide an antenna. The recessed area 50 has a greater depth than recessed area 52. Due to mechanical constraints, it is only possible to have one deeply recessed area where the drill collar inner diameter is substantially reduced. It is within contemplation of the subject invention for the recessed areas 50, 52 to have substantially the same depth or for recessed area 52 to have a greater depth than area 50.

The cylindrical shells of spins in the region of investigation can be segmented axially or, preferably, azimuthally by using at least one directionally sensitive gradient coil 56 arranged in the recessed area 50 and/or 52. In a preferred embodiment of the invention, three gradient coils are positioned circumferentially around the recessed area and separated by an angular distance segment of 120°. Other quantities of gradient coils may be defined, either lesser or greater in number than three, and such coils may be separated by angular distances other than 120° and/or unequal angular segments. Each coil 56 is constructed with loops of wire, which conform to the curvature of the outer surface of the material 54. The magnetic field produced by each gradient coil 56 in a region of the formation facing the coil is substantially parallel to the static magnetic field produced by the magnets.

As is known to those skilled in the art, in the basic NMR measurement, a pulse sequence is applied to the formation under investigation. In U.S. Pat. No. 5,596,274 issued to Abdurrahman Sezginer and U.S. Pat. No. 5,023,551 issued to Kleinberg et al., a pulse sequence, such as the Carr-Purcell-Meiboom-Gill (CPMG) sequence, first applies an excitation pulse, a 90° pulse, to the formation that rotates the spins into the transverse plane. After the spins are rotated by 90° and start to dephase, the carrier of the refocusing pulses, the 180° pulses, is phase shifted relative to the carrier of the 90° pulse sequence according to the following relationship:

$$t_{90°_{\pm x}} - t_0 - [t_{180°_y} - t_1 - \text{echo}_{max}{}^n - t_2]_n,$$

where the bracketed expression is repeated for n=1,2, ... N, where N is the number of echoes collected in a single CPMG sequence and the echo spacing is $t_{echo} = 2t_{cp} = t_{180°_y} + t_1 + t_2$. $90°_{\pm x}$ denotes an RF pulse that causes the spins to rotate by a 90° angle about the ±x-axis, as commonly defined in the rotating frame of magnetic resonance measurements (phase alternated). The time between application of the 90° pulse and the 180° pulse, $t_0$, is less than $t_{cp}$, half the echo spacing. The CPMG sequence enables acquisition of a symmetric measurement (i.e., a measurement without using the gradient coils). The exact timing parameters, $t_0$, $t_1$, and $t_2$, depend on various factors (e.g., the shape of the applied pulses).

In the subject invention, a current pulse applied to gradient coil 56 generates an additional magnetic field, substantially parallel to the static magnetic field. The current pulse is applied between the first 90° and the 180° phase reversing pulse. This additional field causes an additional phase shift for the spins. Since the 180° phase reversing pulse does not compensate for the additional phase shift, the spins subjected to the additional field do not form a spin-echo. However, for spins not subjected to the additional field, a spin-echo occurs at time $2t_{cp}$ with spin-echoes of successively lower amplitude occurring at time $t_{cp}$ after each phase reversing pulse. The pulse sequence is $t_{90°_{\pm x}} - t_0^a - \delta - t_0^b - [t_{180°_y} - t_1 - \text{echo}_{max}{}^n - t_2]_n$, where $t_0^a$ is the time between the 90° pulse and the gradient pulse of duration $\delta$, $t_0^b$ is the time between the gradient pulse and the 180° reversing pulse, and $t_0^a + \delta + t_0^b = t_0$. Due to the succeeding 180°$_y$ pulses and the inhomogeneous fields, the x-component of the NMR signal will decay within a few echoes. Therefore, we focus only on the y-component of the signal. Thus, neglecting relaxation, the first NMR echo signal can be represented as:

$$\text{Signal} = \Im m [\int_{r \in R^3} (M_x^0 + i M_y^0)(r) \exp(-i\gamma G(r) \delta) dc(r)],$$

where i is the imaginary complex unit; $\gamma$ is the gyromagnetic ratio; $M_x^0$ and $M_y^0$ are respectively x and y components of the magnetization at location r at the time of the first echo in the absence of the gradient pulse; $G(r)$ is the component of the gradient field parallel to $\vec{B}_0$ at the same location; $\delta$ is the duration of the gradient pulse; and $dc(r)$ denotes the differential sensitivity of the NMR sonde.

The gradient coils 56 offer a number of advantages for obtaining azimuthal measurements. First, because the axisymmetric antenna detects the spin-echoes, long echo trains can be recorded while the tool rotates in the borehole. Second, the coil 56 simplifies the design of an NMR-LWD tool because the coil 56 does not have the tuning requirements of an RF antenna 36, 38. Third, the same antenna 36, 38 can be used to make symmetric and axisymmetric measurements. Fourth, the coils 56 can be used to obtain NMR measurements with excellent spatial resolution, particularly vertical resolution.

Different modes for obtaining azimuthal NMR measurements are contemplated by the present invention. For example, a "simple spoiling" mode uses at least one coil 56 to spoil the spins in a selected quadrant where a quadrant is defined as an angular distance segment about the periphery of the tool 10, however, more coils 56 may be used to spoil a plurality of quadrants. In either case, two measurements are obtained: a symmetric phase alternated pulse sequence (PAPS) with a fixed wait time followed by a gradient PAPS having a variable wait time, with the selected quadrant spoiled by firing the coil 56 in the quadrant. In a preferred embodiment of the invention, the aforementioned gradient pulse sequence is used. Subtracting the gradient measurement from the symmetric measurement creates the azimuthal measurement. In this mode, one symmetric measurement is obtained for every two PAPS and one azimuthal scan is obtained for every eight PAPS. The measurement noise for the azimuthal measurement is higher than the noise in the symmetric or gradient measurement because the two measurements are combined.

It is possible to reduce the noise contribution by combining different single quadrant spoiling measurements. For example, four gradient PAPS measurements may be obtained by spoiling each quadrant. The measurements are combined to create a synthetic azimuthal and symmetric measurement. By combining measurements made without the gradient coils 56 being fired with measurements made with one or more gradient coils 56 being fired, axially or azimuthally resolved "images" of the formation can be generated. The acquired data, particularly in the form of azimuthal images of porosity and bound fluid, are very desirable for improved petrophysical interpretation in highly deviated and horizontal wellbores and for decision-making while drilling for geologically based wellbore placement.

Optimizing the Pulse Length and Operating Frequency

For a chosen operating RF frequency, there is an optimum duration for the 90° pulse, $t_{90}$, as well as for the 180° pulses, $t_{180}$, which ensures a desired signal-to-noise ratio. The search for an optimal pulse length may be performed during the master calibration of the tool, so that all pulse lengths will be correctly initialized, or when the static magnetic field changes in an unpredictable manner, such as a change due to accumulation of magnetic debris during the drilling process. See U.S. patent application Ser. No. 09/031,926 assigned to Schlumberger Technology Corporation. This technique may also be used to choose the appropriate frequency to meet other criteria, such as keeping the depth of investigation constant.

The optimal pulse length may be determined by measuring the NMR response of a sample using at least two different pulse durations and using a predefined mode independent of the NMR properties of the formation. Alternatively, the optimal pulse length may be determined using at least two different pulse durations and additionally using a mode computed from the NMR properties of the formation. In the first case, stacking the data improves the signal-to-noise ratio, however, the stacking procedure may require a long period of time to acquire data from the formation. Preferably, the measured data are accumulated during a stationary time window when the tool 10 pauses from the drilling operation, such as during the time when a new section of drill pipe is added to the drill string. In the second case, if the $T_2$ distribution of the formation is known, a best acquisition mode may be constructed which provides the largest signal-to-noise ratio for a unit of acquisition time and provides an optimal linear combination of the acquired echoes. Laboratory simulations show that optimum timing for the best acquisition mode is achieved when the duration of the echo train is approximately equal to $T_{2,max}$, the dominate $T_2$ of the formation, and when the wait time, $t_w$, is approximately equal to $2.5 \times T_{2,max}$ (assuming a constant $T_1/T_2$ ratio of 1.5). The best acquisition mode determines the optimal pulse length to within a few percent over several seconds. A similar technique may be used to optimize the NMR signal with respect to the frequency (e.g., saddle point design). The $T_2$ distribution effectively aids the efficient tuning of pulse lengths for the tool 10.

Data Acquisition Modes

As described above, tool 10 has a plurality of antennas 36, 38. In a preferred embodiment of the invention, these antennas 36, 38 do not transmit or acquire data simultaneously. Preferably, after one antenna 36 acquires data, the other antenna 38 experiences a minimum wait time while the power supply recharges in order to transmit the next pulse sequence. It is within contemplation of the subject invention to transmit or acquire data simultaneously. Further, this invention contemplates data acquisition without a requisite wait time.

Based on these design preferences, a plurality of data acquisition modes may be used. By way of example, three representative timings for NMR data acquisition are described below: a fast timing suitable for water-wet sandstone zones, a slow timing appropriate for carbonate zones, and a very slow timing designed for hydrocarbon bearing zones (or invasion of oil based mud). The timings are set forth in Table I.

TABLE I

|  | Wait Time (sec.) | Echo spacing (m sec) | Number of Echoes |
| --- | --- | --- | --- |
| Fast | 2.3 | 0.5 | 400 |
| Slow | 4.6 | 0.5 | 800 |
| very slow | 9.2 | 1.0 | 800 |

Figure 5A:
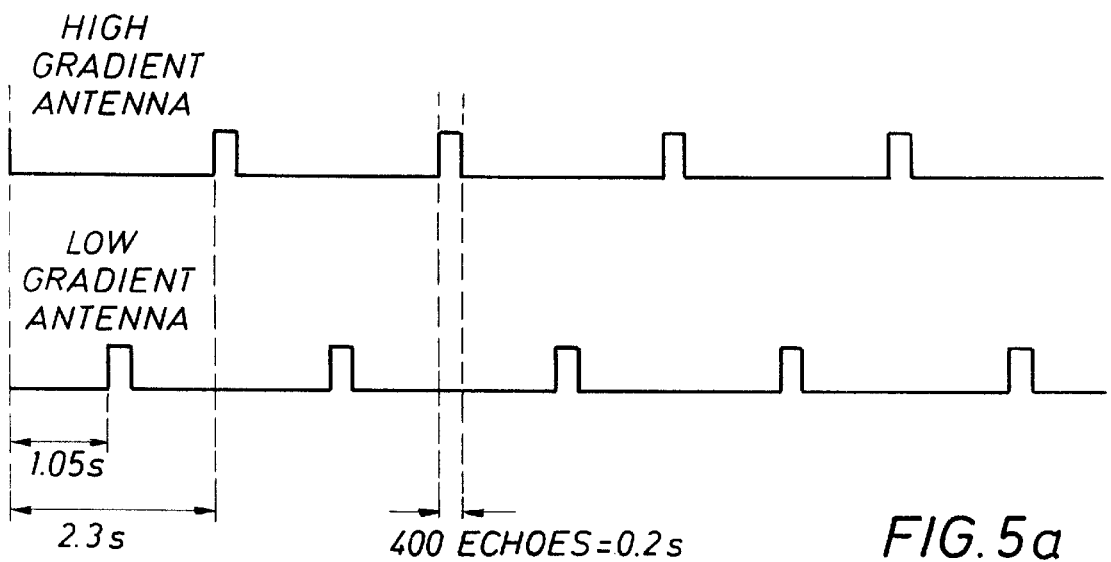
FIG. 5 depicts the simple data acquisition mode.
Figure 5B:
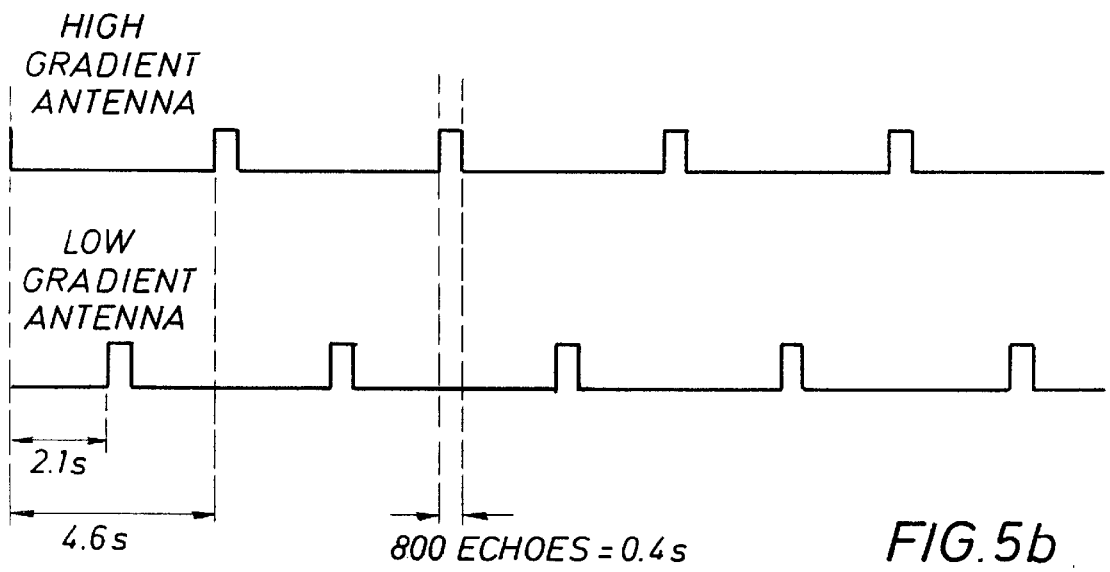
Figure 5C:
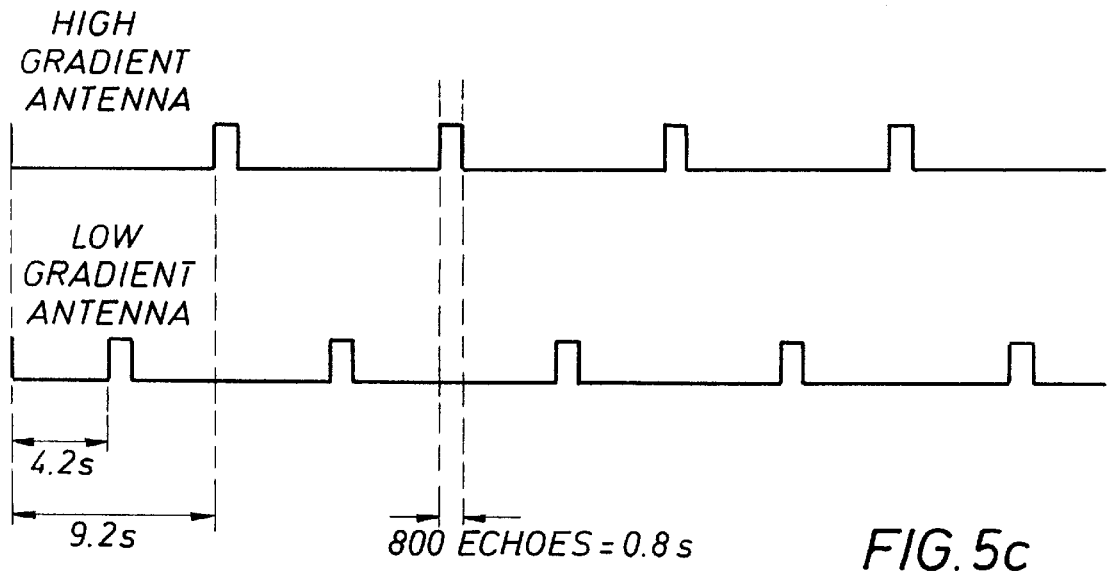

Several different modes may be used with each data acquisition timing, including, but not limited to, the following: simple, interleaved, and bursts. The simplest way to acquire $T_2$ information with the tool 10 is to perform CPMG measurements with both antennas 36, 38 using the same timing. FIG. 5 illustrates the simple data acquisition mode used with the fast decaying, slowly decaying, and very slowly decaying timing from Table I. Each antenna 36, 38 alternately acquires a long pulse sequence which provides an effective porosity measurement from each antenna 36, 38.

Figure 6A:
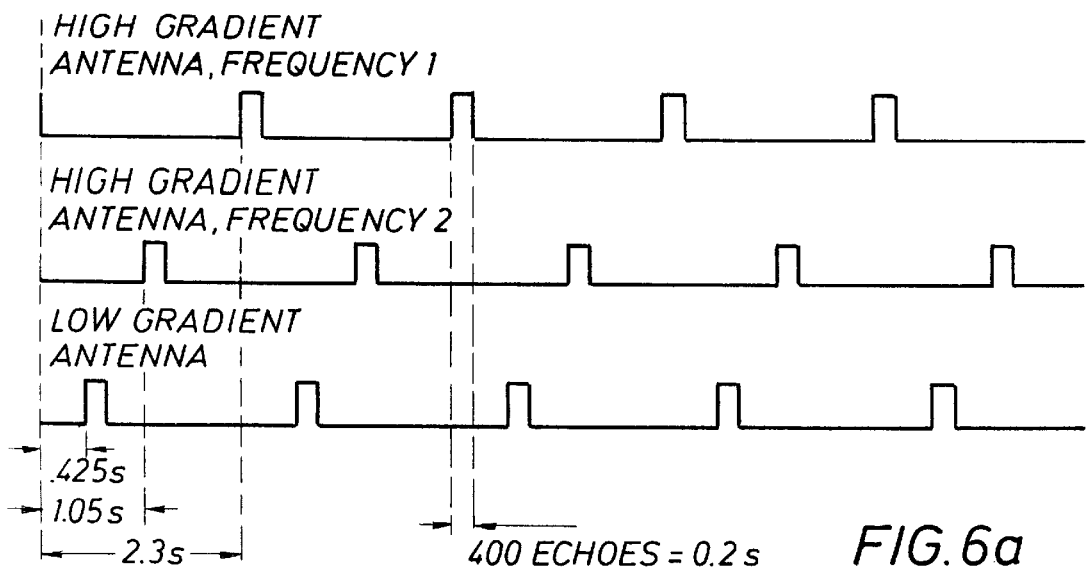
FIG. 6 depicts the interleaved data acquisition mode.
Figure 6B:
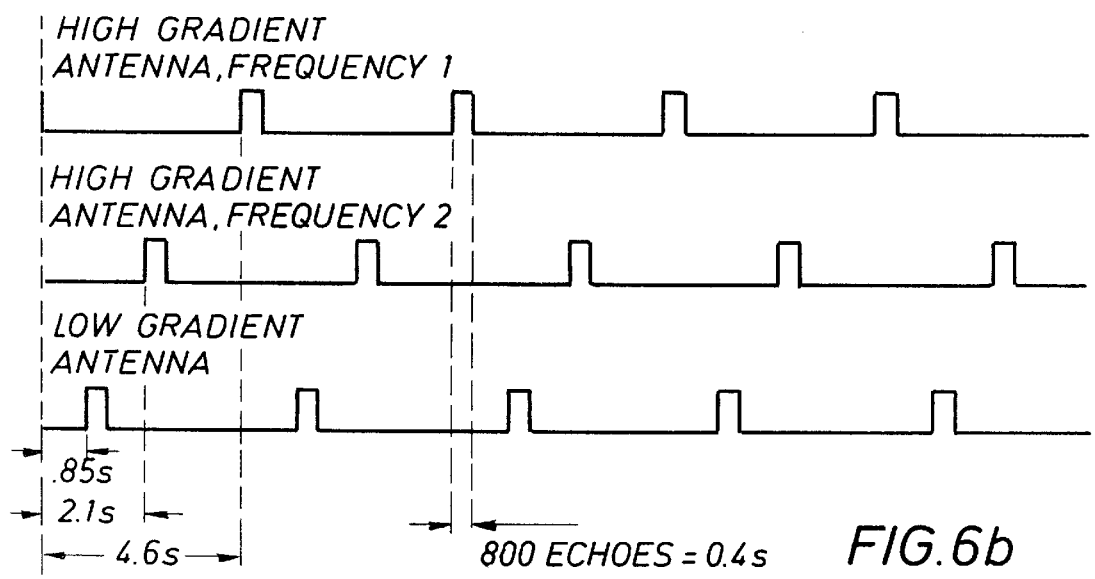
Figure 6C:
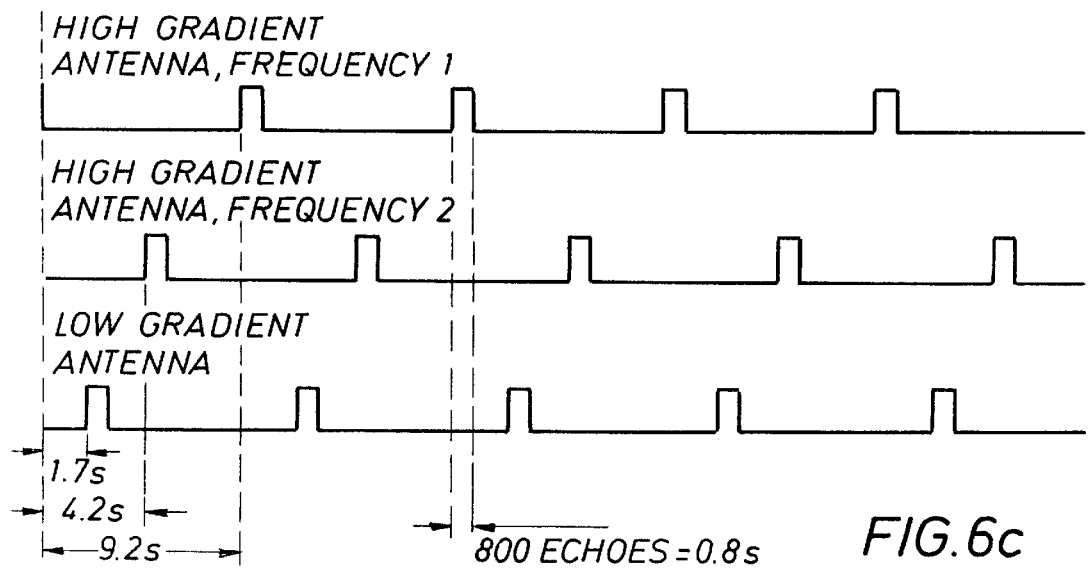

With the interleaved mode, the high gradient antenna measures at least two cylindrical shells at two different frequencies while the low gradient antenna obtains a measurement using a single frequency. FIG. 6 illustrates an interleaved measurement for fast decaying samples, slowly decaying components, and very slowly decaying components using the timing from Table I.

Figure 7A:
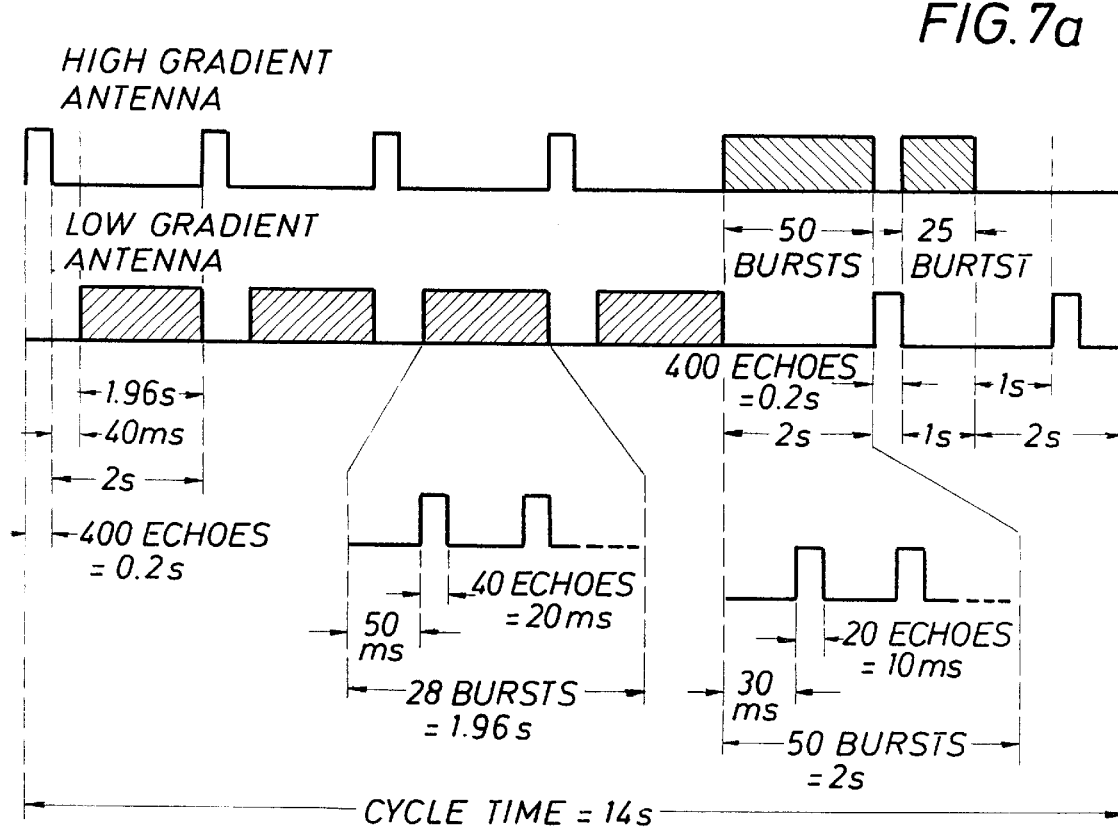
FIG. 7 depicts the burst data acquisition mode.
Figure 7B:
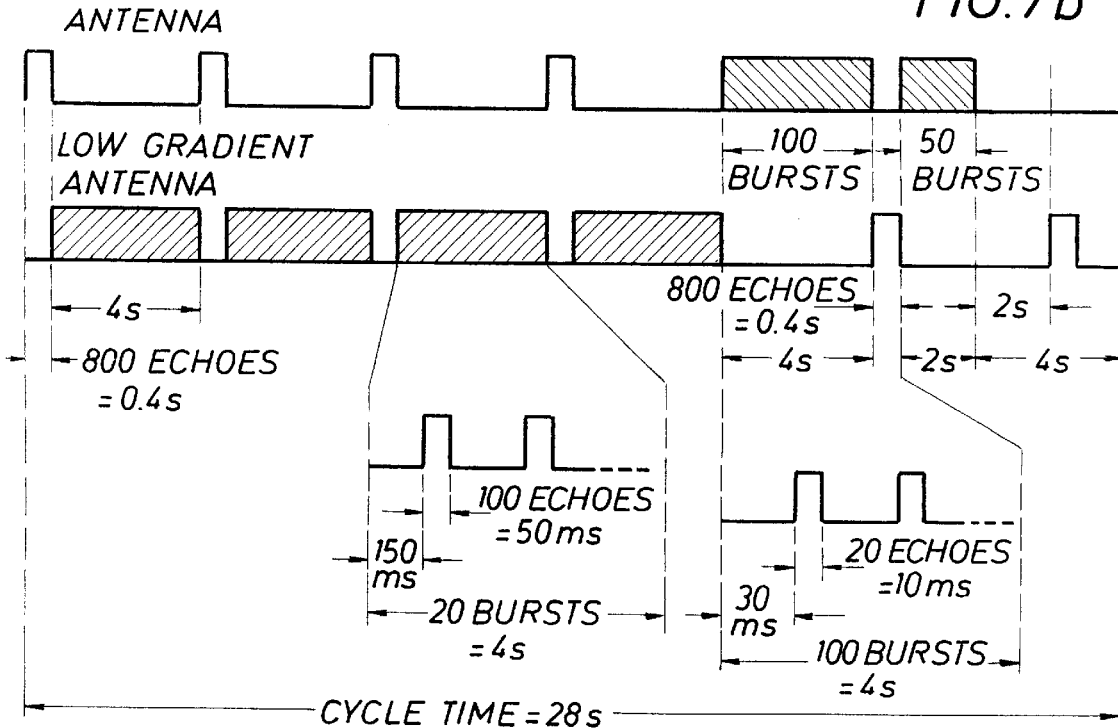
Figure 7C:
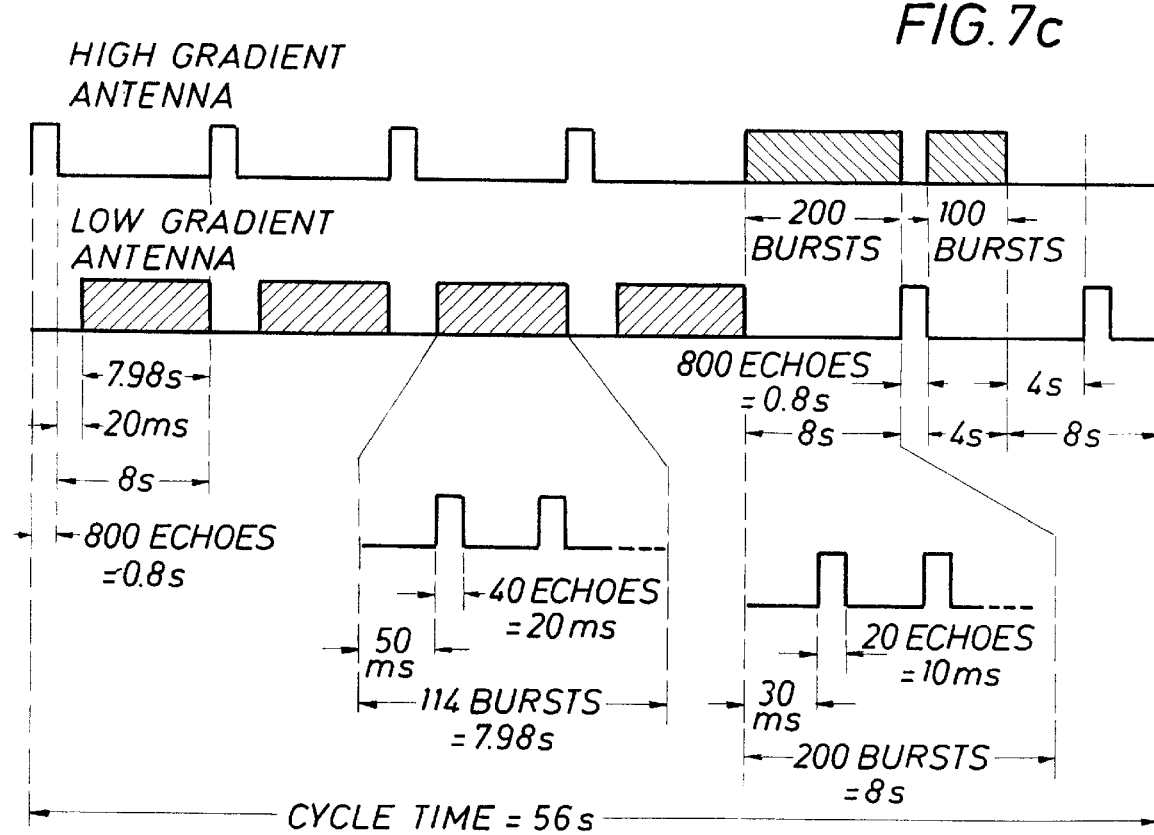

The burst mode enhances the signal-to-noise ratio, especially for the fast decaying components. In addition, the burst mode provides a useful $T_1$ based bound fluid measurement. See WO 98/29639 assigned to Numar Corporation [describes a method for determining longitudinal relaxation times, $T_1$]. Also, see U.S. patent application Ser. No. 09/096, 320 assigned to Schlumberger Technology Corporation [describes a method for polarizing the bound fluid of a formation]. FIG. 7 illustrates burst measurements for fast decaying samples, slowly decaying components, and very slowly decaying components using slightly modified times from Table I.

In addition to the simple, interleaved, and burst modes, with the subject invention, it is possible to optimize formation evaluation measurements by detecting downhole conditions which create a pause during the drilling operation, determining the drilling mode, and using the mode to control data acquisition. Standard rotary drilling operations contain many natural pauses where the tool remains stationary: connection time as a new section of drill pipe is added to the drill string, circulation time when mud is circulated and the drill pipe is possibly rotated, and fishing or jarring time while the drill string is stuck and has to be freed before drilling can resume. These natural pauses, which occur without interrupting normal drilling operations, or deliberately initiated pauses, are utilized to make NMR measurements. The drilling modes include, but are not limited to, drilling, sliding, tripping, circulating, fishing, a short trip (up or down), and drill pipe connections. Determining the drilling mode enhances the ability to obtain NMR measurements that take a long time or that benefit from a quiet environment, e.g., $T_1$, $T_2$, antenna tuning, and hydrocarbon typing. See U.S. pat. app. Ser. No. 09/031,926 assigned to Schlumberger Technology Corporation. It is also possible to adjust acquisition modes based on changes in the environment (e.g., washout, salinity, etc.) and/or changes in the formation NMR properties (e.g., long $T_1$ versus short $T_1$).

The spin-echo amplitudes are obtained by hardware integration of the receiver voltages over a time window. The tool 10 uses phase sensitive detection to measure the in-phase and quadrature components of the spin-echo signal-plus-noise amplitudes. The techniques disclosed in U.S. Pat. No. 5,381,092 issued to Robert Freedman may be used to compute window sums downhole and transmit the window sums to the surface for $T_2$ inversion processing and presentation. Also, the techniques disclosed in U.S. Pat. No. 5,363,041 issued to Abdurrahman Sezginer may be implemented to utilize a linear operator to map a relaxation-time distribution to spin-echoes, produce a singular value decomposition (SVD) of the linear operator, determine vectors of the SVD, and compress the spin-echo data using the vectors. Preferably, the $T_2$ spectrum is computed downhole and transmitted to the surface. This offers the advantage of eliminating a telemetry bottleneck created by transmitting the data required to compute the $T_2$ spectrum to the surface. A digital signal processor may be used to invert the $T_2$ data. The amplitudes, $A_j$, of the spin-echoes are characterized by the following relationship:

$$A_j = \sum_{i=1}^{M} X_{ji} a_i + \eta_j,$$

where $\eta_j$ is the noise in the measurement $A_j$, $a_i$ is the amplitude of the $T_2$ distribution taken at $T_{2,i}$, $$X_{ji} = \exp\left(-\frac{j\Delta t}{T_{2i}}\right)\left(1 - \exp\left(-\frac{t_w}{cT_{2i}}\right)\right)$$

represents the elements of matrix X, where $t_w$ is the wait time and c is a constant (the $T_1/T_2$ ratio), $\Delta t$ is the echo spacing, and j=1,2, . . . N, where N is the number of echoes collected in a single pulse sequence. In matrix notation, the equation becomes $\vec{A} = X\vec{a} + \vec{\eta}$. Since the noise, $\eta$, is unknown, $\vec{a}$ can be approximated by finding a least squares solution, i.e., a minimum of the functional $J = \|\vec{A} - X\vec{a}\|^2$. The solution of this equation is strongly affected by noise present in the data and the solution may have negative components even though the $T_2$ spectrum does not have negative components. To overcome this problem, a regularization term, $\lambda \|\vec{a}\|^2$, is added to the functional and the functional $j_\lambda(\vec{a}) = \|\vec{A} - X\vec{a}\|^2 + \lambda\|\vec{a}\|^2$ is minimized using a suitable iterative minimization algorithm (e.g., Conjugated Gradient Projection Method) under the constraint that $a_i \geq 0$ for i=1 . . . M. See Ron S. Dembo and Ulrich Tulowitzski, *On the Minimization of Quadratic Functions Subject to Box Constraints*, Yale Department of Computer Science (September 1984) (describes the Conjugated Gradient Projection Method). The necessary time for performing the $T_2$ inversion using a digital signal processor is very reasonable. For example, assuming 1800 echoes and 30 samples in the $T_2$ domain, the inversion on a digital signal processor requires less than two seconds.

Pulse Programmer

Figure 8:
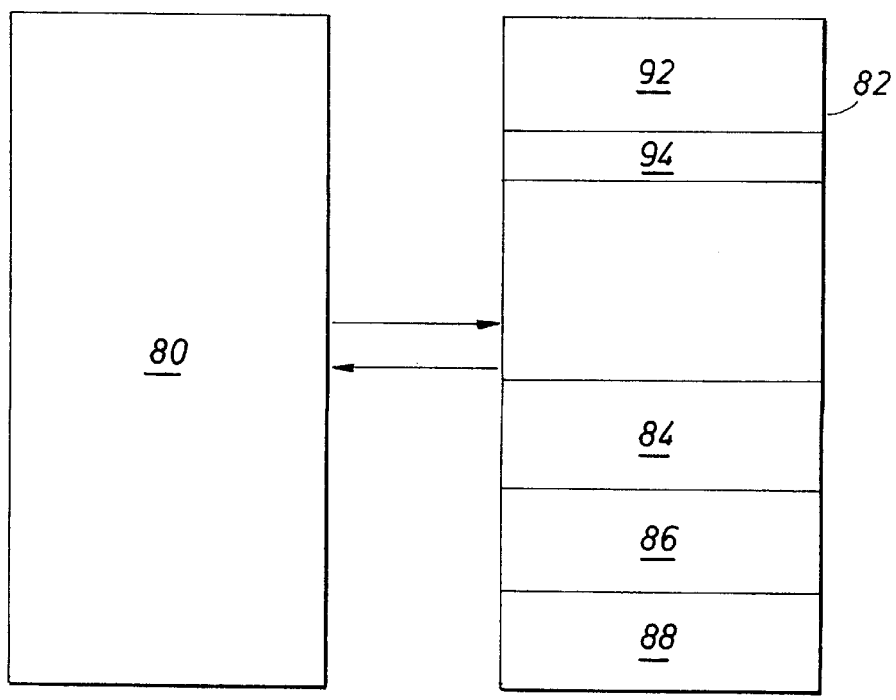
FIG. 8 represents a block diagram of the pulse programmer.

For the basic NMR measurement with tool 10, electronic circuitry applies a pulse sequence to the formation under investigation. Tool 10 includes a pulse programmer 80, which adaptively selects and controls the pulse sequences applied to the formation. The pulse programmer 80 establishes the pulse sequence using information found in the Measurement Control Block 82 (See FIG. 8) and the operating conditions of the tool 10. Preferably, the Measurement Control Block 82 is stored in a downhole memory device. The structure of block 82 is fixed to allow pulse programmer 80 easily to adapt and change the timing of the pulse sequences autonomously downhole. It is advantageous to partition a portion of block 82 into a plurality of tables 84, 86, and 88. Instead of controlling all tool operations that depend on the pulse sequence from the pulse programmer 80, the tables 84, 86, 88 are used to control these operations. This allows the pulse programmer 80 to vary the pulse sequences without introducing contradictions in the tool configuration. The plurality of tables 84, 86, and 88 may include, but are not limited to, the following: a buffer table which describes the layout of stacking buffers, an acquisition table which defines the acquired signals accumulated in buffers, a filter coefficient table which prescribes the detection filter employed with a signal acquisition, a spin dynamics correction table which designates the spin dynamics correction to be used for each buffer, and a data processing table which designates the nuclear magnetic resonance characteristic calculated from the acquired buffers.

The pulse programmer 80 includes a pulse sequence template 94, useful for generating pulse sequences, which comprises a sequence of states dependent on repetition and timing variables. These variables are calculated from sequence configuration parameters using the calculation block 92. The calculation block 92 may be implemented as an executable or interpretive structure. Based on the physical quantity that will be measured, e.g. $T_2$, timing variables may be defined such as the wait time, $t_w$, the echo spacing, $t_{echo}$, and the number of acquired echoes. The configuration parameters include, but are not limited to, $t_{90}$, pulse amplitude, and pulse shape. These parameters may be calculated periodically during calibration of the tool 10 or during operation of the tool 10 since those parameters may vary as the operating conditions of the tool 10 vary. For example, the pulse amplitude and shape depends on the antenna quality factor and, therefore, on the conductivity of the formation surrounding the tool 10.

Normally, after pulse programmer 80 initiates a pulse sequence, the sequence runs deterministically until it is finished. To implement certain azimuthal measurement modes with tool 10, the pulse programmer 80 has the ability to vary the pulse sequence during execution of the sequence. Programmer 80 may stop execution of the pulse sequence and enter a HALT state until an external signal ends the state at time $t_c$ or until a maximum time period, $t_{max}$, has expired. As previously discussed in the Data Acquisition Modes section of this specification, since at least one of the different modes (interleaved) which may be used with the data acquisition timing contemplates interleaving several measurements, the programmer 80 compensates for the time that passed during the HALT state. Preferably, compensation is accomplished by grouping HALT events. For example, a grouping may comprise a pair of HALT events where one HALT event operates as previously described and the other HALT event is a normal event of duration $t_{max}-t_c$. Grouping events allows the programmer 80 to combine sequences having variable and deterministic timing.

In addition, the sequence of states, as defined in the pulse sequence template 94, may comprise several alternatives for parts of the sequence. In real time, one of the alternatives (branching) is chosen dependent on external conditions of the tool (e.g., the azimuth of the tool).

The foregoing description of the preferred and alternate embodiments of the present invention has been presented for purposes of illustration and description. It is not intended to be exhaustive nor to limit the invention to the precise form disclosed. Obviously, many modifications and variations will be apparent to those skilled in the art. The embodiments were chosen and described in order to best explain the principles of the invention and its practical application thereby enabling others skilled in the art to understand the invention for various embodiments and with various modifications as are suited to the particular use contemplated. It is intended that the scope of the invention be defined by the accompanying claims and their equivalents.

What is claimed is:

1. A method for determining a nuclear magnetic resonance property in an investigation region of earth formations surrounding a borehole, comprising the steps of:
    a) generating a substantially axisymmetric static magnetic field into a formation traversed by the borehole with a logging tool;
    b) adaptively controlling the creation and application of a sequence of RF magnetic field pulses to the formation, comprising the steps of:
        i) partitioning a portion of a memory device into a plurality of tables and storing control information in the table;
        ii) determining an operating condition for the tool;
        iii) selecting the sequence of RF magnetic pulses based upon the control information and the operating condition; and,
        iv) defining a template for executing the selected sequence of RF magnetic field pulses; and,
    c) detecting nuclear magnetic resonance signals from the formation.

2. The method of claim 1 further comprising the steps of defining at least one state sequence and storing the state sequences in the template.

3. The method of claim 2 wherein the step of defining at least one state sequence further comprises the step of calculating repetition and timing variables and using the variables to define the state sequences.

4. The method of claim 3 further comprising the step of defining a plurality of configuration parameters and calculating the repetition and timing variables using the configuration parameters.

5. The method of claim 2 further comprising the steps of selecting at least one of the state sequences and executing the selected state sequences.

6. The method of claim 1 further comprising the steps of defining a plurality of alternate state sequences and storing the alternate state sequences in the template.

7. The method of claim 6 further comprising the steps of selecting at least one or the alternate state sequences and executing the selected alternate state sequence.

8. The method of claim 6 further comprising the steps of determining an operating environment condition, selecting it least one of the alternate state sequences, and executing the selected alternate state sequence.

9. The method of claim 1 further comprising the step of executing the sequence of RF magnetic field pulses deterministically through completion of the sequence.

10. The method of claim 9 further comprising the step of varying the sequence of RF magnetic field pulses during execution of the sequence.

11. The method of claim 10 further comprising the step of halting execution of the sequence for a period of time.

12. The method of claim 11 further comprising the steps of resuming execution of the sequence and compensating for the period of time.

13. The method of claim 1 further comprising the steps of selecting at least one table and distributing the table containing the control information to an external task during execution of the pulse sequence.

14. The method of claim 1 further comprising the steps of selecting at least one table ad distributing the table containing the control information to an external task before or after executing the pulse sequence.

15. The method of claim 7 further comprising the step of selecting the alternate state sequence while executing the sequence of RF magnetic field pulses.

16. The method of claim 15 further comprising the step of executing the selected alternate state sequence.

17. An apparatus for determining a nuclear magnetic resonance property in an investigation region of earth formations surrounding a borehole, comprising:
    a) a logging tool having at least one magnet for generating a substantially axisymmetric static magnetic field into a formation traversed by the borehole;
    b) a pulse programmer for adaptively controlling the creation and application of a sequence of RF magnetic field pulses to the formation, comprising:
        i) a memory device, means for partitioning a portion of the memory device into a plurality of tables, and means for storing control information in the tables;
        ii) means for determining an operating condition for the tool;
        iii) means for selecting the sequence of RF magnetic pulses based upon the control information and the operation condition;
        iv) means for defining a template for executing the sequence of RF magnetic field pulses; and
    e) means for detecting nuclear magnetic resonance signals from the formation.

18. The apparatus of claim 17 further comprising means for defining at least one state sequence and means for storing the state sequences in the template.

19. The apparatus of claim 18 further comprising means for calculating repetition and timing variables and means for using the variables to define the state sequences.

20. The apparatus of claim 19 further comprising means for defining a plurality of configuration parameters and means for calculating repetition and timing variables using the configuration parameters.

21. The apparatus of claim 18 further comprising means for selecting at least one of the state sequences and means for executing the selected state sequences.

22. The apparatus of claim 17 further comprising means for defining a plurality of alternate state sequences and means for storing the alternate state sequences in the template.

23. The apparatus of claim 22 further comprising means for selecting at least one of the alternate state sequences and means for executing the selected alternate state sequence.

24. The apparatus of claim 22 further comprising means for determining an operating environment condition, means for selecting at least one of the alternate state sequences, and means for executing the selected alternate state sequence.

25. The apparatus of claim 17 further comprising means for executing the sequence of RF magnetic field pulses deterministically through completion of the sequence.

26. The apparatus of claim 25 further comprising means for varying the sequence of RF magnetic field pulses during execution of the sequence.

27. The apparatus of claim 26 further comprising means for halting execution of the sequence for period of time.

28. The apparatus of claim 27 further comprising means for resuming execution of the sequence and means for compensating for the period of time.

29. The apparatus of claim 19 wherein the means for calculating repetition and timing variables comprises an executable or interpretive structure.

* * * * *